(12) United States Patent
Nishizawa et al.

(10) Patent No.: US 10,539,511 B2
(45) Date of Patent: Jan. 21, 2020

(54) DETECTION METHOD, INSPECTION METHOD, DETECTION APPARATUS, AND INSPECTION APPARATUS

(71) Applicant: Lasertec Corporation, Yokohama (JP)

(72) Inventors: Masayasu Nishizawa, Yokohama (JP); Tsunehito Kohyama, Yokohama (JP); Hironobu Suzuki, Yokohama (JP)

(73) Assignee: Lasertec Corporation, Yokohama (JP)

( * ) Notice: Subject to any disclaimer, the term of this patent is extended or adjusted under 35 U.S.C. 154(b) by 0 days.

(21) Appl. No.: 16/186,227

(22) Filed: Nov. 9, 2018

(65) Prior Publication Data

US 2019/0204235 A1 Jul. 4, 2019

(30) Foreign Application Priority Data

Dec. 28, 2017 (JP) ................. 2017-253050

(51) Int. Cl.
*G01N 21/88* (2006.01)
*G01N 21/956* (2006.01)

(52) U.S. Cl.
CPC ....... *G01N 21/8806* (2013.01); *G01N 21/956* (2013.01); *G01N 2021/95676* (2013.01); *G01N 2201/0636* (2013.01)

(58) Field of Classification Search
CPC ... G01N 21/8806; G01N 21/88; G01N 21/956
(Continued)

(56) References Cited

U.S. PATENT DOCUMENTS 5,486,701 A * 1/1996 Norton ............... G01B 11/0625
250/372
5,608,526 A * 3/1997 Piwonka-Corle .... G01N 21/211
356/369

(Continued)

FOREIGN PATENT DOCUMENTS

JP   H11311608 A   11/1999
JP   2005241290 A   9/2005
(Continued)

OTHER PUBLICATIONS

Japanese Patent Office, Office Action Issued in Application No. 2017-253050, dated Aug. 28, 2018, 5 pages.

*Primary Examiner* — Roy M Punnoose
(74) *Attorney, Agent, or Firm* — McCoy Russell LLP

(57) ABSTRACT

A detection method, an inspection method, a detection apparatus, and an inspection apparatus capable of preventing an error in a luminance unevenness correction and thereby accurately inspecting an object to be inspected are provided. A detection method according to the present disclosure includes illuminating an object to be inspected by using illumination light including pulsed light, acquiring image data of the object to be inspected by concentrating light from the object to be inspected illuminated by the illumination light and detecting the concentrated light by an inspection detector, acquiring image data of a luminance distribution of the illumination light, the luminance distribution being detected by illuminating a correction detector by using part of the illumination light, and detecting inspection image data by correcting the image data of the object to be inspected based on the image data of the luminance distribution.

18 Claims, 17 Drawing Sheets

(58) Field of Classification Search
USPC .................................................. 356/239.3
See application file for complete search history.

(56) References Cited

U.S. PATENT DOCUMENTS

| | | | |
|---|---|---|---|
| 7,349,079 B2* | 3/2008 | Zhao | G01N 21/211 |
| | | | 356/128 |
| 2003/0137662 A1* | 7/2003 | Janik | G01N 21/211 |
| | | | 356/369 |
| 2005/0196059 A1 | 9/2005 | Inoue et al. | |
| 2007/0030948 A1* | 2/2007 | Singer | G03F 7/70083 |
| | | | 378/34 |
| 2009/0040513 A1 | 2/2009 | Abe et al. | |
| 2010/0060890 A1 | 3/2010 | Tsuchiya et al. | |
| 2015/0146200 A1* | 5/2015 | Honda | G01N 21/956 |
| | | | 356/237.5 |
| 2016/0091797 A1* | 3/2016 | Ryzhikov | G03F 7/70058 |
| | | | 355/67 |
| 2018/0276812 A1* | 9/2018 | Kohyama | G06T 7/0008 |

FOREIGN PATENT DOCUMENTS

| | | | |
|---|---|---|---|
| JP | 2009075068 A | 4/2009 | |
| JP | 2010091552 A | 4/2010 | |
| JP | 6249513 B1 | 12/2017 | |

\* cited by examiner

DETECTION METHOD, INSPECTION METHOD, DETECTION APPARATUS, AND INSPECTION APPARATUS

CROSS REFERENCE TO RELATED APPLICATIONS

The present application claims priority to Japanese Patent Application No. 2017-253050, filed on Dec. 28, 2017. The entire contents of the above-cited application are hereby incorporated by reference for all purposes.

BACKGROUND

The present disclosure relates to a detection method, an inspection method, a detection apparatus, and an inspection apparatus. In particular, the present disclosure relates to a detection method and a detection apparatus for detecting image data that is used for an inspection of an object to be inspected, and an inspection method and an inspection apparatus for inspecting the object to be inspected by using the detected image data for the inspection.

For example, in an inspection for inspecting a mask for EUV (Extreme Ultra Violet) lithography (hereinafter, referred to as a EUV mask), high-intensity pulsed light may be used in order to improve the accuracy of the inspection. Further, critical illumination may be used in order to secure the luminance of illumination light. The critical illumination is a method in which an object is illuminated so that an image of a light source is formed on a top surface of a EUV mask, and uses an optical system capable of illuminating the object with high luminance.

Further, in some cases, when image data for an inspection (hereinafter also referred to as inspection image data) is detected, an XY-direction two-dimensional area sensor is operated in a TDI (Time Delay Integration) mode in which pixel values of the area sensor are transferred in an X-direction while being synchronized with the stage and time delay integration is performed for the obtained pixel values. The use of the TDI mode can compensate for insufficient sensitivity of sensor elements and hence a mask pattern can be photographed with high sensitivity.

A lithography mask inspection apparatus compares a taken inspection image with design data or a reference image that is obtained by photographing (hereinafter also expressed as shooting) the same pattern on a sample. Then, when they do not match each other, the inspection apparatus determines that there is a pattern defect.

When a pulsed light source is used as a light source for an inspection apparatus, in many cases, a luminance distribution of pulsed light emitted from the light source changes from one pulse to another and hence variations occur. Note that the term "variations" in this specification means not only that the total amount of light of pulsed light changes from one pulse to another, but also that a positional distribution of irradiation light intensities on a surface irradiated with pulsed light (hereinafter simply referred to as a luminance distribution) changes from one pulse to another. Such variations are called luminance unevenness.

When there is luminance unevenness in illumination light emitted from a pulsed light source, undesired changes in the luminance (artifacts) occur in a taken mask pattern image according to the luminance unevenness and hence an error occurs in the determination of a pattern defect. Therefore, it is necessary to detect luminance unevenness of the light source and correct output fluctuations of the TDI sensor according to the detected luminance unevenness.

Regarding the change in the total light amount of pulsed light from one pulse to another, as described in Japanese Unexamined Patent Application Publication No. 2010-091552, it is possible to correct output fluctuations of the TDI sensor by installing a correction light amount sensor that detects a light amount of pulsed light and measuring the total light amount of each pulse in synchronization with the cycle of the pulsed light. However, in this document, since the change in the luminance distribution from one pulse to another is not taken into consideration, there is a problem that an artifact caused by this change cannot be corrected.

In order to correct luminance unevenness, it is necessary not only to measure the total light amount of each pulse, but also to use a detector for correction (hereinafter also referred to as a correction detector) capable of detecting a luminance distribution of pulsed lights. Therefore, as a detection apparatus for correcting luminance unevenness, the following method is conceivable. That is, luminance unevenness is corrected by detecting a luminance distribution of a light source using a second TDI sensor.

However, as explained later with reference to examples, in the case in which image data of an object to be inspected and image data of a luminance distribution are acquired by using a TDI sensor, when the number of pixels in a transfer direction in a detector for inspection (hereinafter also referred to as an inspection detector) differs from the number of pixels in a correction detector, there is a possibility that an error is involved due to a difference between the numbers of pulses of light emitted within a cumulative time period of these detectors.

The present disclosure has been made to solve the above-described problem and an object thereof is to provide a detection method, an inspection method, a detection apparatus, and an inspection apparatus capable of preventing an error in a luminance unevenness correction and thereby accurately inspecting an object to be inspected.

SUMMARY

A first exemplary aspect is a detection method including: illuminating an object to be inspected by using illumination light including pulsed light; acquiring image data of the object to be inspected by concentrating light from the object to be inspected illuminated by the illumination light and detecting the concentrated light by an inspection detector; acquiring image data of a luminance distribution of the illumination light, the luminance distribution being detected by illuminating a correction detector by using part of the illumination light; and detecting inspection image data by correcting the image data of the object to be inspected based on the image data of the luminance distribution. By the above-described configuration, it is possible to accurately detect image data of the object to be inspected.

Further, a magnification of the image data of the luminance distribution is made lower than a magnification of the image data of the object to be inspected. In this way, it is possible to increase a light amount with which the luminance distribution is detected and thereby to accurately correcting the luminance distribution of the illumination light.

A light emission timing of a light source that emits pulsed light is controlled so that it does not coincide with a transfer timing of the inspection detector and the correction detector. That is, synchronization control is performed so that the transfer timing of the inspection detector and the correction detector and the light emission timing of the pulsed light source have a certain phase difference therebetween. By performing this synchronization control, it is possible to prevent or minimize an error that would otherwise occur due to the below-described difference between the numbers of pulses of light emitted within a cumulative time period of the detectors.

The number of pixels in the transfer direction (hereinafter also referred to as a transfer direction pixel number) $P_{TC}$ and a transfer cycle $\tau_{TC}$ of the correction detector are determined so that relations $P_{TC}=M_C \times N$ and $\tau_{TC}=\tau_S/M_C$ are satisfied, where: $\tau_S$ is a light emission cycle of the pulsed light; N is the number of times the pulsed light is emitted within a cumulative time period of image data of the inspection detector; and $M_C$ is an integer. In this way, it is possible to prevent or minimize an error that would otherwise occur due to the difference between the numbers of pulses of light emitted within the cumulative time period.

A transfer direction pixel number $P_{TI}$ and a transfer cycle $\tau_{TI}$ of the inspection detector are determined so that relations $P_{TI}=R \times M_C \times N$ and $\tau_{TI}=\tau_S/(M_C \times R)$ are satisfied, where R is the magnification of the image data of the object to be inspected relative to the magnification of the image data of the luminance distribution. In this way, it is possible to prevent or minimize an error that would otherwise occur due to the difference between the numbers of pulses of light emitted within the cumulative time period.

Further, in the acquiring of the image data of the luminance distribution of the illumination light, part of the illumination light is taken out between a dropping mirror and a reflecting mirror by using a cut mirror, the dropping mirror being configured to make the illumination light incident on the object to be inspected, the reflecting mirror being configured to convert the illumination light into converged light and make the converged light incident on the dropping mirror. In this way, it is possible to prevent or minimize the influence on the illumination light used for the inspection and thereby to accurately inspect the object.

Further, in a cross-sectional area in a cross section of the illumination light perpendicular to its optical axis in a place where the cut mirror is disposed, a cross-sectional area of the part of the illumination light is made smaller than a cross-sectional area of the other part of the illumination light. In this way, it is possible to prevent or minimize the influence on the illumination light used for the inspection and thereby to accurately inspect the object.

The transfer direction pixel numbers of the inspection detector and the correction detector are adjusted by using a light-shielding plate attached to a fine positioner. In this way, it is possible to accurately set the transfer direction pixel numbers and thereby to prevent or minimize an error in the luminance unevenness correction.

Further, the above-described detection method further includes, after the detecting of the inspection image data, inspecting the object to be inspected by using the inspection image data. In this way, it is possible to accurately inspect the object to be inspected.

Another exemplary aspect is a detection apparatus including: an illumination optical system configured to illuminate an object to be inspected by using illumination light including pulsed light; a detection optical system configured to acquire image data of the object to be inspected by concentrating light from the object to be inspected illuminated by the illumination light and detecting the concentrated light by an inspection detector; a monitor unit configured to acquire image data of a luminance distribution of the illumination light, the luminance distribution being detected by illuminating a correction detector by using part of the illumination light; and a processing unit configured to detect inspection image data by correcting the image data of the object to be inspected based on the image data of the luminance distribution. By the above-described configuration, it is possible to accurately detect image data of the object to be inspected.

Further, a magnification of the image data of the luminance distribution acquired by the monitor unit is made lower than a magnification of the image data of the object to be inspected acquired by the detection optical system. In this way, it is possible to increase an amount of light with which the luminance distribution is detected and thereby to accurately correcting the luminance distribution of the illumination light.

Regarding a light emission timing of a light source that emits pulsed light, synchronization control is performed so that the light emission timing does not coincide with a transfer timing of the inspection detector and the correction detector. That is, the light emission timing is controlled so that the transfer timing of the inspection detector and the correction detector and the light emission timing of the pulsed light source have a certain phase difference therebetween. In this way, it is possible to prevent or minimize an error that would otherwise occur due to the below-described difference between the numbers of pulses of light emitted within the cumulative time period of the detectors.

Further, a transfer direction pixel number $P_{TC}$ and a transfer cycle $\tau_{TC}$ of the correction detector satisfy relations $P_{TC}=M_C \times N$ and $\tau_{TC}=\tau_S/M_C$, where: $\tau_S$ is a light emission cycle of the pulsed light; N is the number of times the pulsed light is emitted within a cumulative time period of image data of the inspection detector; and $M_C$ is an integer. In this way, it is possible to prevent or minimize an error that would otherwise occur due to the difference between the numbers of pulses of light emitted within the cumulative time period.

A transfer direction pixel number $P_{TI}$ and a transfer cycle $\tau_{TI}$ of the inspection detector satisfy relations $P_{TI}=R \times M_C \times N$ and $\tau_{TI}=\tau_S/(M_C \times R)$, where R is the magnification of the image data of the object to be inspected relative to the magnification of the image data of the luminance distribution. In this way, it is possible to prevent or minimize an error that would otherwise occur due to the difference between the numbers of pulses of light emitted within the cumulative time period.

Further, the illumination optical system includes a dropping mirror configured to make the illumination light incident on the object to be inspected, and a reflecting mirror configured to convert the illumination light into converged light and make the converged light incident on the dropping mirror. Further, the monitor unit includes a cut mirror configured to take out part of the illumination light between the reflecting mirror and the dropping mirror. In this way, it is possible to prevent or minimize the influence on the illumination light used for the inspection and thereby to accurately inspect the object.

Further, in a cross-sectional area in a cross section of the illumination light perpendicular to its optical axis in a place where the cut mirror is disposed, a cross-sectional area of the part of the illumination light is made smaller than a cross-sectional area of the other part of the illumination light. In this way, it is possible to prevent or minimize the influence on the illumination light used for the inspection and thereby to accurately inspect the object.

The detection apparatus further includes a light-shielding unit configured to adjust the transfer direction pixel numbers of the inspection detector and the correction detector by using a light-shielding plate attached to a fine positioner. In this way, it is possible to accurately set the transfer direction pixel numbers and thereby to prevent or minimize an error in the luminance unevenness correction.

Further, an inspection apparatus includes the above-described the detection apparatus, in which the processing unit inspects the object to be inspected by using the detected inspection image data. In this way, it is possible to accurately inspect the object to be inspected.

According to the present disclosure, it is possible to provide a detection method, an inspection method, a detection apparatus, and an inspection apparatus capable of preventing an error in a luminance unevenness correction and thereby accurately inspecting an object to be inspected.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

A specific configuration of this embodiment is explained hereinafter with reference to the drawings. Embodiments according to the present disclosure are shown in the following descriptions. However, the scope of the present disclosure is not limited to the below-shown embodiments. In the following descriptions, components/structures to which the same symbols are assigned are substantially similar to each other.

First Embodiment

An inspection apparatus and an inspection method according to a first embodiment are described. Firstly, the inspection apparatus is described. After that, the inspection method using the inspection apparatus will be described.

(Configuration of Inspection Apparatus)

Figure 1:
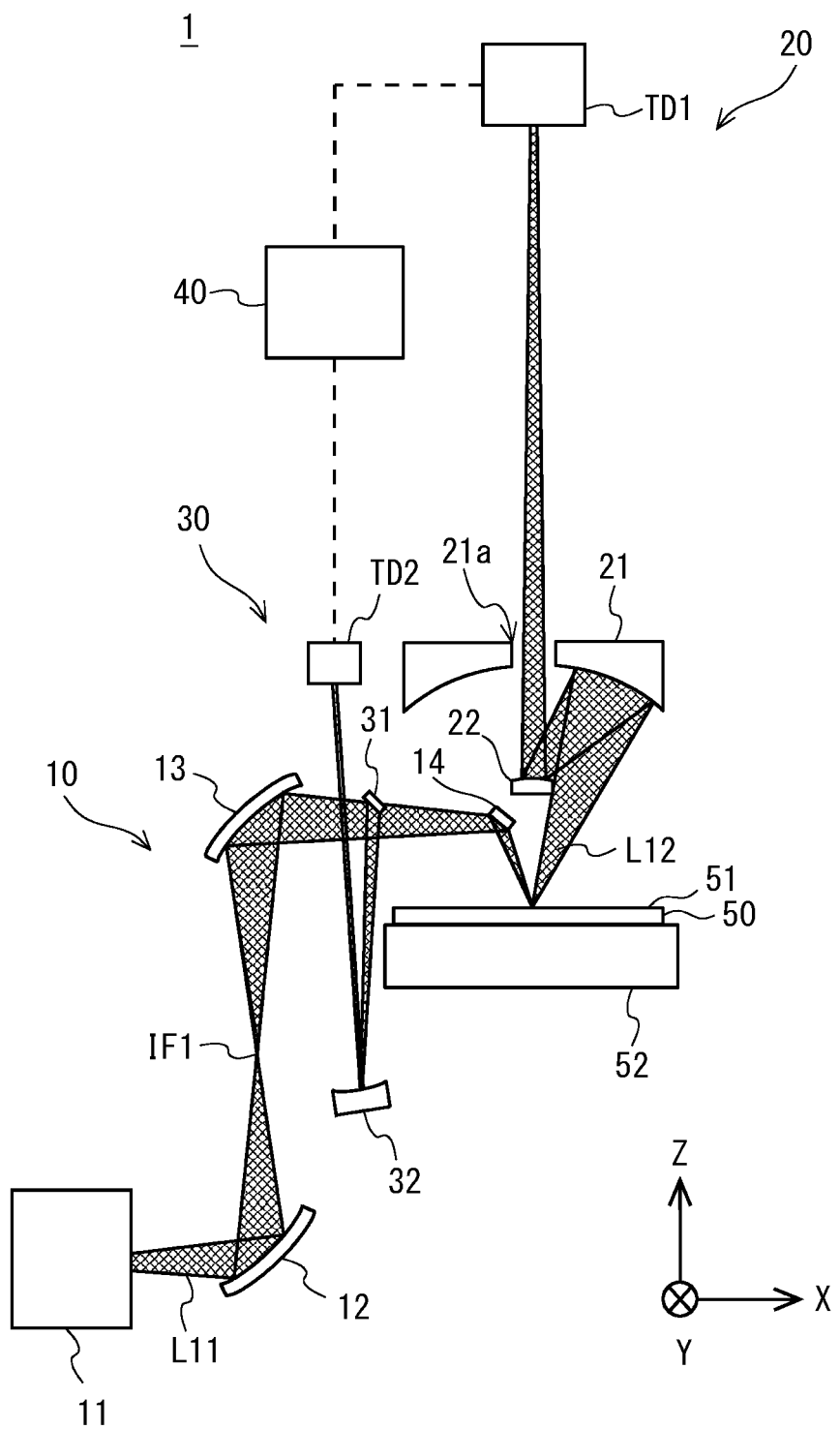
FIG. 1 shows an example of a configuration of an inspection apparatus according to a first embodiment.

A configuration of an inspection apparatus according to this embodiment is described. FIG. 1 shows an example of the configuration of the inspection apparatus according to the embodiment. As shown in FIG. 1, the inspection apparatus 1 includes an illumination optical system 10, a detection optical system 20, a monitor unit 30, and a processing unit 40. The illumination optical system 10 includes a light source 11, an ellipsoidal mirror 12, an ellipsoidal mirror 13, and a dropping mirror 14. The detection optical system 20 includes a concave mirror 21 with a hole formed therein (hereinafter referred to as a holed concave mirror 21), a convex mirror 22, and an inspection detector TD1. The holed concave mirror 21 and the convex mirror 22 form a Schwarzschild magnification optical system. The monitor unit 30 includes a cut mirror 31, a concave mirror 32, and a correction detector TD2.

The inspection apparatus 1 detects inspection image data and inspects an object to be inspected (hereinafter also referred to as an inspection target) by using the detected inspection image data. Since the inspection apparatus 1 detects inspection image data, it is also considered to be a detection apparatus that detects inspection image data. The inspection target is, for example, a EUV mask 50. Note that the inspection target is not limited to the EUV mask 50.

The light source 11 generates illumination light L11 including pulsed light. The light source 11 periodically emits pulsed light. The light emission cycle of the pulsed light is represented by $\tau_S$. The illumination light L11 may contain, for example, EUV light having a wavelength of 13.5 [nm], which is the same wavelength as an exposure wavelength for the EUV mask 50, i.e., for the inspection target. The illumination light L11 generated by the light source 11 is reflected on the ellipsoidal mirror 12. The illumination light L11 reflected on the ellipsoidal mirror 12 travels while becoming narrower (i.e., while its cross section is becoming smaller) and is concentrated at a focal point IF1. The focal point IF1 is positioned in a place conjugate with an upper surface 51 of the EUV mask 50.

After passing through the focal point IF1, the illumination light L11 travels while spreading (i.e., while its cross section is becoming larger) and is incident on a reflecting mirror such as the ellipsoidal mirror 13. The illumination light L11 incident on the ellipsoidal mirror 13 is reflected thereon and travels while becoming narrower. Then, the narrowed illumination light L11 is incident on the dropping mirror 14.

That is, the ellipsoidal mirror 13 converges the illumination light L11 and makes the converged light incident on the dropping mirror 14. The dropping mirror 14 is disposed right above the EUV mask 50. The illumination light L11, which has been incident on the dropping mirror 14 and reflected thereon, is incident on the EUV mask 50. That is, the dropping mirror 14 makes the illumination light L11 incident on the EUV mask 50.

The ellipsoidal mirror 13 concentrates the illumination light L11 onto the EUV mask 50. The illumination optical system 10 may be configured so that when the illumination light L11 illuminates the EUV mask 50, an image of the light source 11 is formed on the upper surface 51 of the EUV mask 50. In such a case, the illumination optical system 10 provides critical illumination. In this way, the illumination optical system 10 illuminates the inspection target by using the illumination light L11 including pulsed light generated by the light source 11. The illumination optical system 10 may illuminate the inspection target by using the critical illumination by the illumination light L11. Note that the illumination optical system 10 may illuminate the inspection target without using the critical illumination.

The EUV mask 50 is disposed on a stage 52. Note that a plane parallel to the upper surface 51 of the EUV mask 50 is defined as an XY-plane and a direction perpendicular to the XY plane is defined as a Z-direction. The illumination light L11 enters (i.e., incident on) the EUV mask 50 in a direction inclined from the Z-direction. That is, the illumination light L11 obliquely enters (i.e., is obliquely incident on) the EUV mask 50 and illuminates the EUV mask 50.

The stage 52 is an XYZ-drive stage. By moving the stage 52 in XY-directions, a desired area on the EUV mask 50 is illuminated. Further, a focus can be adjusted by moving the stage 52 in the Z-direction.

The illumination light L11 emitted from the light source 11 illuminates an inspection area on the EUV mask 50. The inspection area illuminated by the illumination light L11 is, for example, an area of 0.5 [mm] square. Reflected light L12, i.e., the light that has been incident on the EUV mask 50 in the direction inclined from the Z-direction and reflected thereon, is incident on the holed concave mirror 21. A hole 21a is formed at the center of the holed concave mirror 21.

The reflected light L12 reflected on the holed concave mirror 21 is incident on the convex mirror 22. The convex mirror 22 reflects the reflected light L12 coming from the holed concave mirror 21 toward the hole 21a of the holed concave mirror 21. The reflected light L12, which has passed through the hole 21a, is detected by the inspection detector TD1.

The inspection detector TD1 is, for example, a detector including a TDI sensor and acquires image data of the inspection target, i.e., the EUV mask 50. The inspection detector TD1 includes a plurality of pixels arranged in a line in one direction. Linear image data taken by the plurality of pixels arranged in a line is referred to as one-dimensional image data. The inspection detector TD1 acquires a plurality of one-dimensional image data by performing scanning in a direction perpendicular to the one direction.

The inspection detector TD1 accumulates optical energy received within an exposure time period in a given pixel as an electrical charge and transfers the accumulated electrical charge to the next pixel during a transfer operation. Then, in the pixel to which the electrical charge has been transferred, optical energy is further accumulated as an electrical charge. The above-described operation is repeated. The direction in which the electrical charge is transferred is referred to as a transfer direction. The inspection detector TD1 periodically transfers an electrical charge in the transfer direction. The cycle at which the inspection detector TD1 transfers an electrical charge is referred to as a transfer cycle $\tau_{TT}$. The number of pixels in the transfer direction in the inspection detector TD1 is referred to as a transfer direction pixel number $P_{TT}$. The TDI sensor includes, for example, a CCD (Charge Coupled Device). Note that the TDI sensor is not limited to those including CCDs.

As described above, the detection optical system 20 concentrates the reflected light L12 from the inspection target illuminated by the illumination light L11 and acquires image data of the inspection target by detecting the concentrated reflected light L12 by the inspection detector TD1. The image data is, for example, one-dimensional image data.

The reflected light L12 contains information on a defect on the EUV mask 50 and the like. Specular reflection light of the illumination light L11, which has been incident on the EUV mask 50 in the direction inclined from the Z-direction, is detected by the detection optical system 20. When there is a defect on the EUV mask 50, the defect is observed as a dark image. Such an observation method is called a bright-field observation. The plurality of one-dimensional image data of the EUV mask 50 acquired by the inspection detector TDI are output to the processing unit 40 and processed into two-dimensional image data there.

Figure 2:
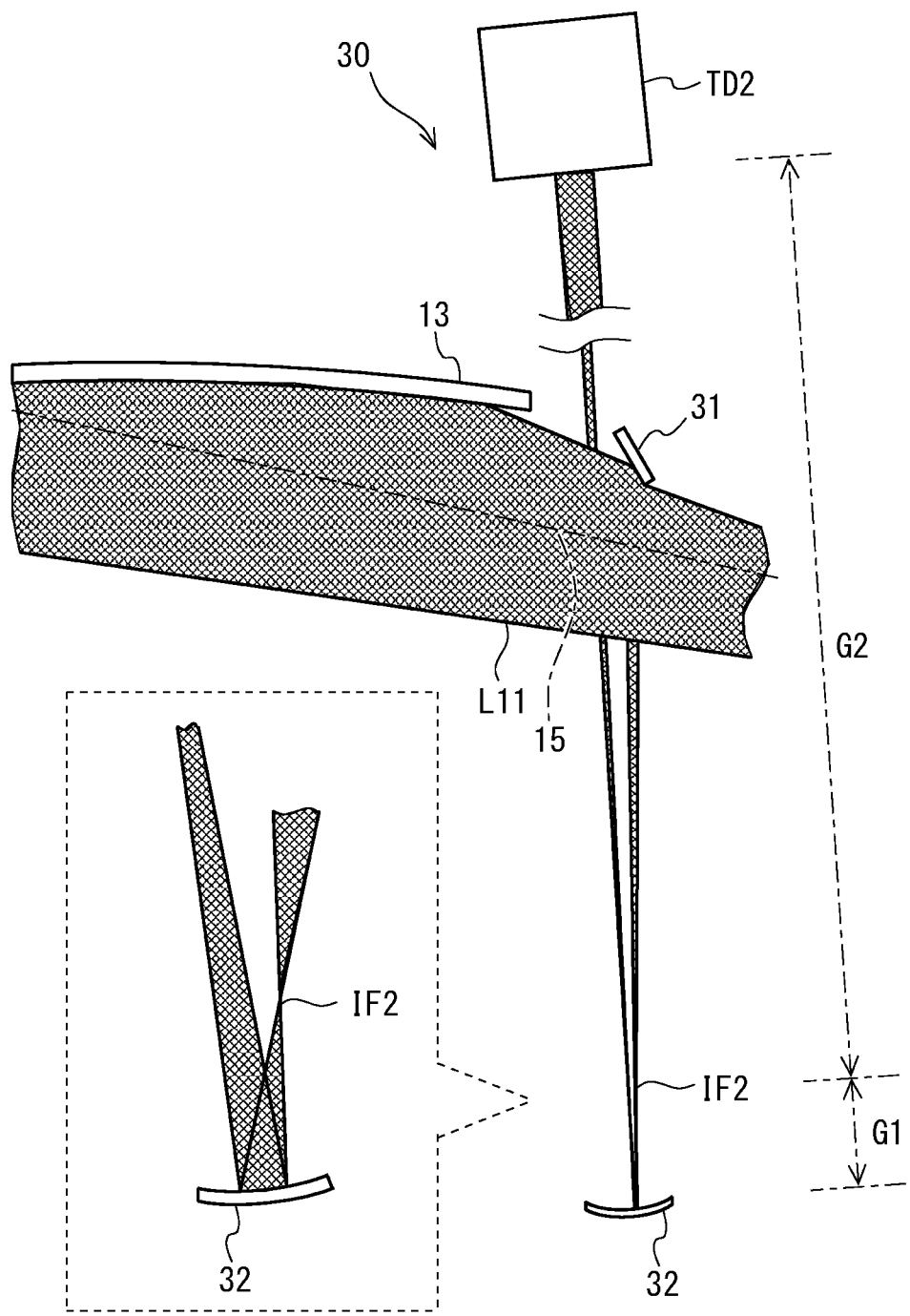
FIG. 2 is a configuration diagram showing an example of a monitor unit in the inspection apparatus according to the first embodiment.

FIG. 2 is a configuration diagram showing an example of the monitor unit 30 in the inspection apparatus 1 according to the first embodiment. FIG. 2 also shows an enlarged view of the concave mirror 32 and the periphery thereof. As shown in FIGS. 1 and 2, the cut mirror 31 of the monitor unit 30 is disposed between the ellipsoidal mirror 13 and the dropping mirror 14, and takes out part of the illumination light L11 between the ellipsoidal mirror 13 and the dropping mirror 14. The cut mirror 31 reflects a small part of the beam of the illumination light L11 so that the small part is cut out from the illumination light L11. The part of the beam is, for example, an upper part of the beam.

In a cross-sectional area of a cross section of the illumination light L11 perpendicular to an optical axis 15 thereof at a place where the cut mirror 31 is disposed, a cross-sectional area of the part of the illumination light L11 reflected by the cut mirror 31 is smaller than that of the remaining part of the illumination light L11.

For example, when the cross-sectional area of the cross section perpendicular to the optical axis 15 of the illumination light L11 at the place where the cut mirror 31 is disposed is 100, the cross-sectional area of the taken-out part is about 1. The angle for taking out the part of the illumination light L11 which is taken out from the light source 11 in the direction perpendicular to the optical axis 15 is, for example, ±7 [°]. The angle of the illumination light L11 used for the EUV mask 50 is, for example, in the range of ±6 [°]. Only the upper part of the beam of the illumination light L11 in the range of, for example, 1 [O] is taken out by the cut mirror 31 in order to use it in the monitor unit 30. Even when the upper part of the beam is slightly taken out as described above, the amount of the illumination light L11 incident on the EUV mask 50 barely decreases. Therefore, it is possible to minimize the deterioration of the accuracy of the inspection.

The cut mirror 31 is disposed in, for example, a place close to a pupil in the illumination optical system 10. By taking out the part of the illumination light L11 by the cut mirror 31 in the place close to the pupil in the illumination optical system 10, it is possible to obtain an excellent correlation between image data acquired by the inspection detector TD1 and image data acquired by the correction detector TD2. The inspection detector TDI and the correction detector TD2 may include respective TDI sensors having the same pixel size.

The illumination light L11, which has been reflected on the cut mirror 31, travels while becoming narrower and is concentrated at a focal point IF2. After that, the illumination light L11 travels while spreading and is incident on the concave mirror 32.

The concave mirror 32 and a plurality of mirrors (not shown) enlarge the part of the illumination light L11 taken out by the cut mirror 31. Here, a distance between the focal point IF2 and the concave mirror 32 is represented by a distance G1 and a distance between the focal point IF2 and the correction detector TD2 is represented by a distance G2. Image data acquired by the correction detector TD2 can be magnified. However, in order to obtain a high magnification (up to 500), the distance G2 is greatly increased. For example, when the distance G1 is set to 5 [mm] or shorter, the distance G2 is set to 2,500 [mm] or shorter. In this way, a magnification of 500 times is obtained. For example, a magnification of 500 times can be obtained by using a plurality of mirrors.

In this embodiment, the magnification of the image data of the luminance distribution acquired by the monitor unit 30 is lower than that of the image data of the inspection target acquired by the detection optical system 20. A solid angle necessary for taking out part of the light is equivalent to the square of the magnifications ratio. For example, when the magnification of the inspection detector TDI is 20 times and the magnification of the correction detector TD2 is 2 times, the solid angle necessary for taking out the part of the light by using the cut mirror 31 is one hundredth ($1/100$) of the solid angle for taking out the light from the light source 11. When expressed by the NA, it is one tenth ($1/10$). Note that the magnification of image data of the luminance distribution acquired by the monitor unit 30 may be the same as the magnification of image data of the inspection target acquired by the detection optical system 20.

The illumination light L11, which has been incident on the concave mirror 32 and reflected thereon, is detected by the correction detector TD2. The correction detector TD2 is, for example, a detector including a TDI sensor and acquires image data of a luminance distribution of the illumination light L11. The correction detector TD2 includes a plurality of pixels arranged in a line in one direction. Similarly to the inspection detector TD1, linear image data taken by the plurality of pixels arranged in a line is referred to as one-dimensional image data. The correction detector TD2 acquires a plurality of one-dimensional image data by performing scanning in a direction perpendicular to the one direction.

The cycle at which the correction detector TD2 performs a transfer is referred to as a transfer cycle $\tau_{TC}$. The number of pixels in the transfer direction in the correction detector TD2 is referred to as a transfer direction pixel number $P_{TC}$. The TDI sensor includes, for example, a CCD. Note that the TDI sensor is not limited to those including CCDs.

The monitor unit 30 acquires image data of a luminance distribution of the illumination light L11 that is detected by irradiating the correction detector TD2 by using part of the illumination light L11. For example, an optical system may be disposed (or configured) so that an image of the light source 11 of the illumination light L11 is formed on the correction detector TD2. In this way, the monitor unit 30 acquires image data of the luminance distribution of the illumination light L11 that is detected by critical illumination using part of the illumination light L11. In this way, it is possible to accurately correct the luminance distribution. Note that the monitor unit 30 may acquire image data of the luminance distribution of the illumination light L11 without using the critical illumination. The image data of the luminance distribution of the illumination light L11 acquired by the correction detector TD2 is output to the processing unit 40.

The processor 40 is connected to the detection optical system 20 and the monitor unit 30 through signal lines or wirelessly. The processing unit 40 receives image data of the inspection target from the inspection detector TDI of the detection optical system 20. Further, the processing unit 40 receives image data of the luminance distribution of the illumination light L11 from the correction detector TD2 of the monitor unit 30.

The processing unit 40 detects inspection image data by correcting the image data of the EUV mask 50 acquired by the detection optical system 20 based on the image data of the luminance distribution acquired by the monitor unit 30. Therefore, the inspection apparatus 1 can be regarded as an inspection apparatus 1 including a detection apparatus. Further, the processing unit 40 inspects the EUV mask 50 based on the inspection image data of the EUV mask 50 that has been detected by performing the correction.

(Inspection Method)

Figure 3:
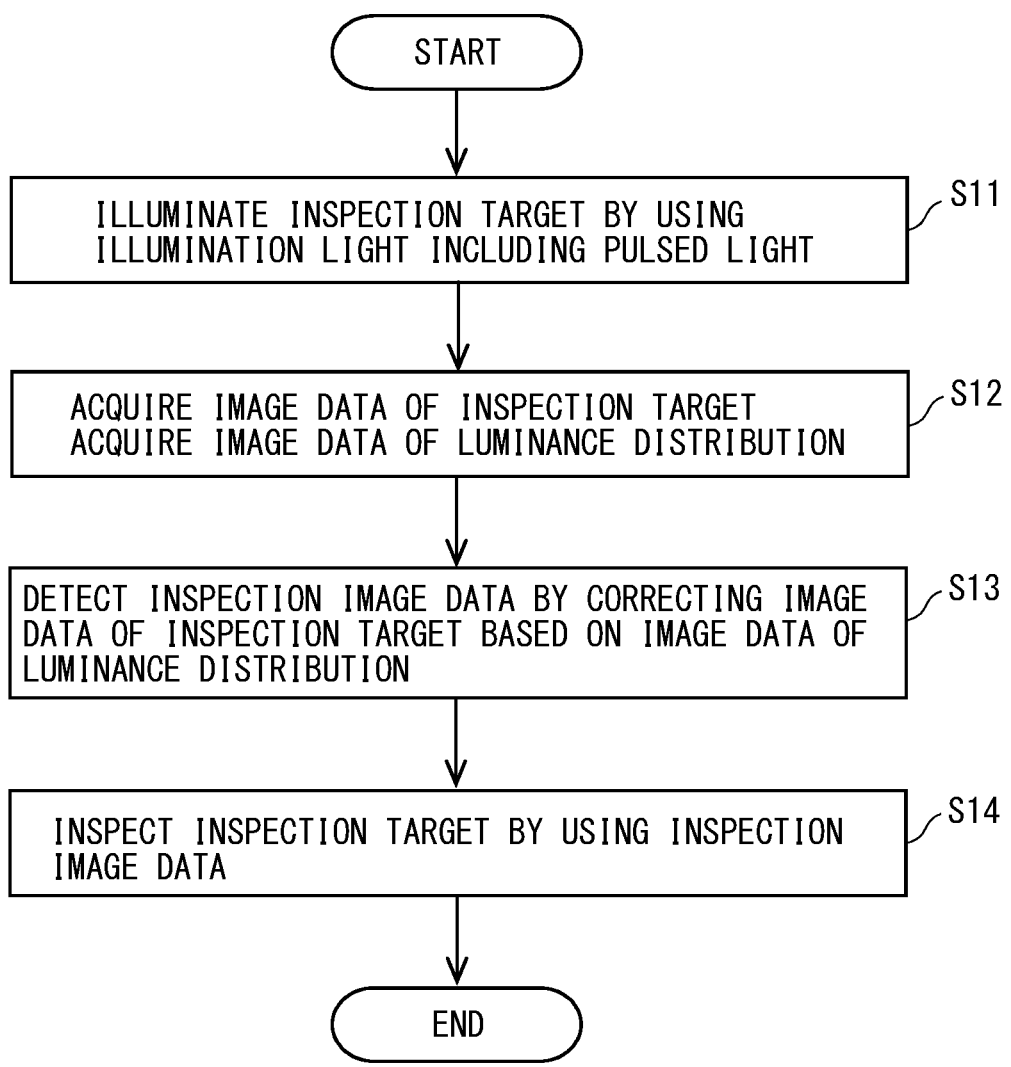
FIG. 3 is a flowchart showing an example of an inspection method according to the first embodiment.

Next, as an operation performed by the inspection apparatus 1 according to the first embodiment, an inspection method using the inspection apparatus 1 is described. FIG. 3 is a flowchart showing an example of an inspection method according to the first embodiment.

As shown in a step S11 in FIG. 3, firstly, an inspection target is illuminated by using illumination light including pulsed light. Specifically, for example, a EUV mask 50 is illuminated by illumination light L11 including pulsed light generated by the light source 11. In this case, the illumination optical system 10 may be configured so that the EUV mask 50 is illuminated by critical illumination. Then, the EUV mask 50 is illuminated by the illumination light L11.

Next, as shown in a step S12 in FIG. 3, image data of the inspection target and image data of a luminance distribution of the illumination light L11 are acquired. Specifically, for example, inspection image data is acquired by concentrating light from the inspection target illuminated by the illumination light L11 and detecting the concentrated light by the inspection detector TD1. Further, image data of the luminance distribution of the illumination light L11, which is detected by irradiating the correction detector TD2 with part of the illumination light L11, is acquired.

Next, as shown in a step S13 in FIG. 3, inspection image data is detected by correcting the image data of the inspection target based on the image data of the luminance distribution. Specifically, the processing unit 40 divides (i.e., arithmetically divides) the image data of the inspection target output from the inspection detector TD1 by the corresponding image data of the luminance distribution output from the correction detector TD2. In this way, the processing unit 40 detects the inspection image data in which luminance unevenness has been corrected.

When each of the inspection detector TD1 and the correction detector TD2 includes a TDI sensor, the image data of each of the inspection detector TD1 and the correction detector TD2 is accumulated signals of pulsed lights that are emitted within its cumulative time period. Therefore, it is desirable that the image data of the inspection detector TD1, in which luminance unevenness should be corrected, and the image data of the correction detector TD2, which is used to detect the luminance unevenness, be obtained by accumulating signals of the same number of pulsed lights.

To make the numbers of pulsed lights emitted within the cumulative time period of the inspection detector TD1 and the correction detector TD2 equal to each other at all times, it is necessary that a light emission cycle $\tau_S$ of pulsed light of the light source 11, transfer cycles $\tau_{TI}$ and $\tau_{TC}$ in the inspection detector TD1 and the correction detector TD2, and transfer direction pixel numbers $P_{TI}$ and $P_{TC}$ of the inspection detector TD1 and the correction detector TD2 have a specific relation among them.

In the following description, it is assumed that the inspection detector TD1 and the correction detector TD2 use respective TDI sensors having the same pixel size. Under this condition, a condition for ensuring that the inspection detector TD1 and the correction detector TD2 acquire image data through irradiation of the same number of pulsed lights at all times is examined hereinafter.

Firstly, a case in which the transfer direction pixel numbers $P_{TI}$ and $P_{TC}$ of the inspection detector TD1 and the correction detector TD2 are equal to each other is examined. In this case, the numbers of pulsed lights emitted within the cumulative time period of the inspection detector TD1 and the correction detector TD2 are always equal to each other. Therefore, an error in inspection image data that is detected by correcting image data of the inspection target based on image data of the luminance distribution is small.

However, in the case in which the transfer direction pixel numbers $P_{TI}$ and $P_{TC}$ of the inspection detector TD1 and the correction detector TD2 differ from each other, an error could occur due to the difference between the numbers of pulses of light emitted within the cumulative time period of the inspection detector TD1 and the correction detector TD2. Therefore, unless some countermeasures are taken, there is a possibility that the error included in the inspection image data increases.

Note that the inspection detector TD1 and the correction detector TD2 including TDI sensors are collectively referred to as TDI detectors. The error caused by the luminance unevenness correction increases when the light emission cycle $\tau_S$ of the light source 11 is longer than the transfer cycle $\tau_T$ of the TDI detector. In the following description, it is assumed that the light emission cycle $\tau_S$ of the light source 11 is longer than the transfer cycle $\tau_T$ of the TDI detector.

The TDI detector accumulates optical energy received within an exposure time period in a given pixel as an electrical charge and transfers the accumulated electrical charge to the next pixel during a transfer operation. Then, in the pixel to which the electrical charge has been transferred, optical energy is further accumulated as an electrical charge. The above-described operation is repeated.

In the case in which the light source 11 that emits pulsed light is used, if the transfer operation of the TDI detector and the emission of pulsed light occur at the same timing, the electrical charge accumulated by the received light is distributed to two pixels. Therefore, in order to maintain the numbers of pulsed lights emitted within the cumulative time period of the inspection detector TD1 and the correction detector TD2 unchanged, it is necessary to make the light source 11 emit light while controlling its light emission timing so that the light emission timing does not coincide with the transfer timing of the inspection detector TD1 and the correction detector TD2.

Figure 4:
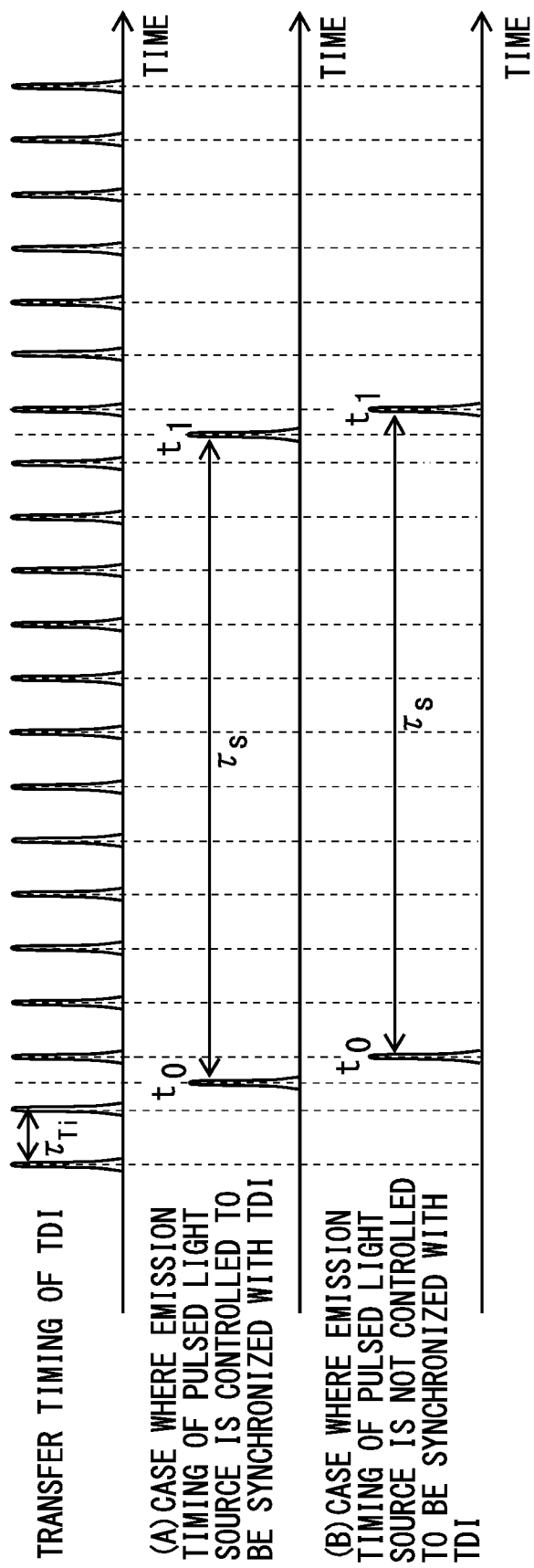
FIG. 4 shows an example of a transfer timing of a TDI sensor and a light emission timing of a light source that emits pulsed light.

FIG. 4 shows an example of a transfer timing of the TDI detector and a light emission timing of the light source that emits pulsed light. FIG. 4(A) shows an example in which times t0 and t1 at which pulsed lights are emitted are controlled so that they do not coincide with the transfer timing of the TDI detector. For example, timing control is performed so that there are exactly twelve transfer timings during the light emission cycle $\tau_S$ of the pulsed light. That is, synchronization control is performed so that the light emission timing of the light source 11 and the transfer timings of the inspection detector TD1 and the correction detector TD2 have a certain phase difference therebetween.

If the light emission timing of pulsed light is not controlled, there is a possibility that a transfer by the TDI detector and a light emission of pulsed light occur at the same timing as shown in FIG. 4 (B). When the transfer by the TDI detector and the light emission timing occur at the same timing, the electrical charge, which is supposed to be accumulated in one pixel, is divided and distributed to two pixels. When this phenomenon occurs at the first pixel in the transfer direction in the TDI sensor or at the last pixel in the transfer direction in the TDI sensor, part of the electrical charge, which is supposed to be accumulated in the pixel of the TDI detector, is lost. In other words, the effective number of pulses accumulated in the pixel becomes a value smaller than one. As a result, an error occurs in the correction of the luminance and the luminance distribution.

Figure 5:
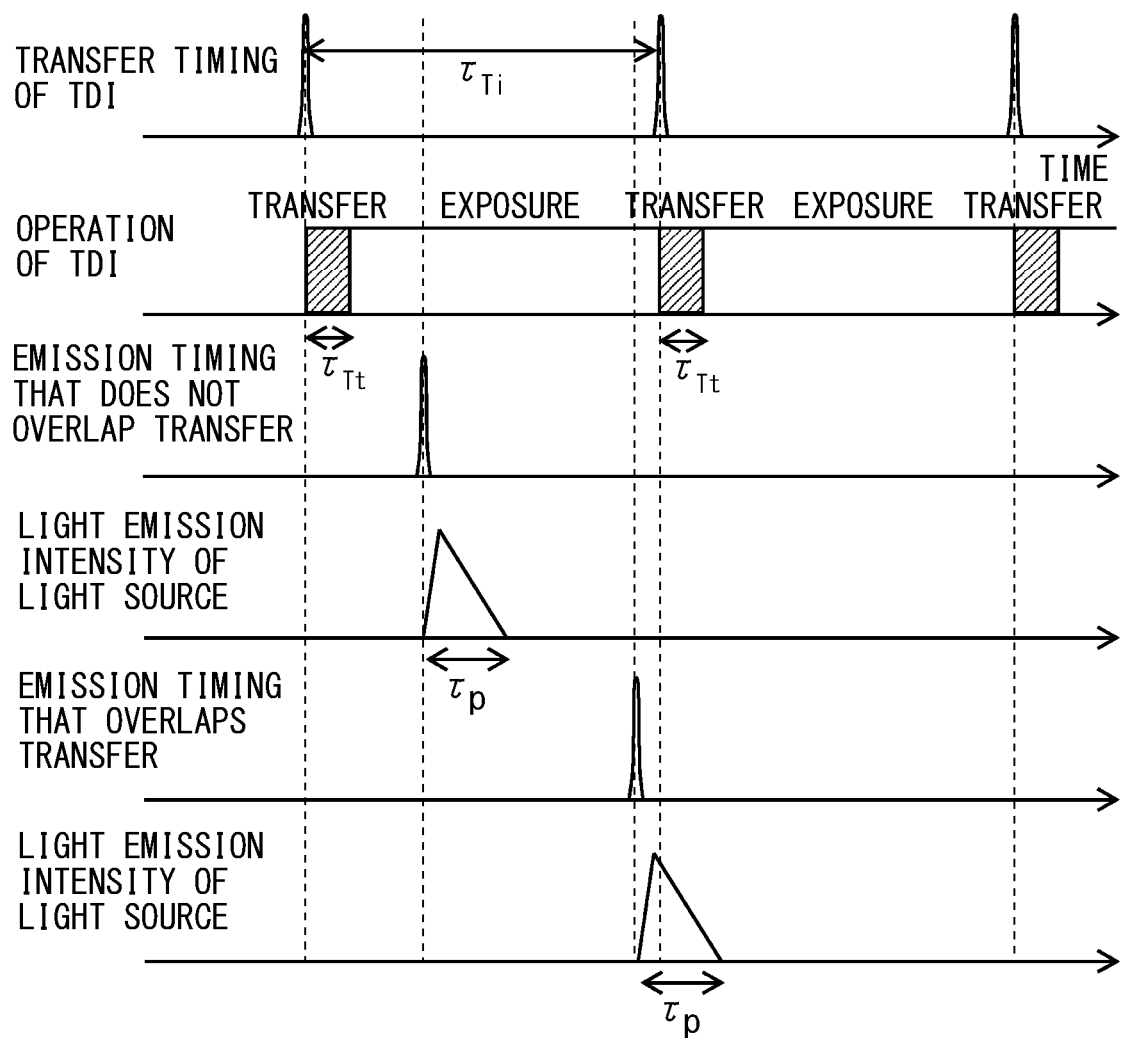
FIG. 5 shows an example of a transfer timing of a TDI sensor, an operation of the TDI sensor, a light emission timing of a light source, and light emission intensity of the light source.

FIG. 5 shows an example of a transfer timing of the TDI sensor, an operation of the TDI sensor, a light emission timing of the light source, and light emission intensity of the light source. As shown in FIG. 5, when clock pulses indicating transfer timings are input to the TDI sensor, the TDI sensor starts a transfer operation. The cycle of the clock pulse indicating the transfer timing of the TDI sensor is a transfer cycle $\tau_T i$. The transfer operation of the TDI sensor requires a transfer time $\tau_{Tt}$.

The transfer timing of the TDI sensor and the light emission timing of the light source are controlled so that they have a certain phase difference therebetween. That is, a clock pulse indicating the light emission timing triggers the light source to generate pulsed light with a phase difference (a small time difference) with respect to the clock pulse indicating the transfer timing. The duration of pulsed light is a duration $\tau_p$. Therefore, the transfer time $\tau_{Tt}$ and the duration $\tau_p$ do not overlap each other.

In contrast, in the case in which the light source emits illumination light including pulsed light at timings that are not synchronized with the transfer timing, the light emission timing of pulsed light could overlap the transfer timing of the TDI sensor. Specifically, the transfer time $\tau_{Tt}$ and the duration $\tau_p$ overlap each other. When the transfer timing of the TDI sensor and the light emission timing of pulsed light overlap each other as described above, the amount of light, which is supposed to be accumulated in one pixel, is divided and distributed to two pixels. As a result, there is a possibility that an error may be included in the correction of the luminance and the luminance distribution.

To avoid this error, the light emission cycle $\tau_S$ of pulsed light of the light source 11 needs to be synchronized with the transfer cycle $\tau_T$ of the TDI detector so that they do not overlap each other. Therefore, the following condition needs to be satisfied. That is, as a condition 1, the light emission cycle $\tau_S$ of the light source should be an integral multiple of the transfer cycle $\tau_T$ of the TDI detector as shown in the below-shown Expression (1). In the expression, M is an integer.

$$\tau_S = M \times \tau_T \quad (1)$$

The condition 1 may also be expressed as follows. That is, the light source 11 emits light every time the TDI detector performs transfers M times.

Further, in order to ensure that image data is acquired by illuminating an object by a certain number of pulsed lights (i.e., the same number of pulsed light) at all times, the following condition has to be satisfied. That is, as a condition 2, the cumulative time period $\tau_I$ of the TDI detector should be an integral multiple of the light emission cycle $\tau_S$ of the light source as shown in the below-shown Expression (2). In the expression, N is an integer.

$$\tau_I = N \times \tau_S \quad (2)$$

The condition 2 may also be expressed as follows. That is, the light source 11 emits light exactly N times within the cumulative time period $\tau_I$ of image data of the TDI detector.

When the cumulative time period $\tau_I$ of the TDI sensor is not an integral multiple of the emission cycle $\tau_S$ of the light source, the remainder of a division of the cumulative time period $\tau_I$ of the TDI detector by the light emission cycle $\tau_S$ of the light source does not become zero. In this case, image data that is obtained by accumulating signals of the number of illumination pulses equal to the quotient and image data that is obtained by accumulating signals of the number of illumination pulses larger than the quotient by one are periodically (i.e., alternately) output.

Note that the cumulative time period $\tau_I$ of the TDI detector is the product of the transfer direction pixel number $P_T$ and the transfer cycle $\tau_T$ of the TDI detector.

$$\tau_I = P_T \times \tau_T \quad (3)$$

Therefore, the below-shown Expression (4) is derived from the Expressions (2) and (3).

$$P_T \times \tau_T = N \times \tau_S \quad (4)$$

As a result, the below-shown Expression (5) is obtained.

$$\tau_S = (P_T/N) \times \tau_T \quad (5)$$

By comparing the Expressions (1) and (5), the below-shown Expression (6) is derived.

$$P_T = M \times N \quad (6)$$

That is, for satisfying the condition 2, the transfer direction pixel number $P_T$ of the TDI detector has to be M times (M is an integer) the number N of pulses that are emitted within the cumulative time period of the TDI detector.

Next, a case in which the transfer direction pixel number $P_{TI}$ of the inspection detector TD1 differs from the transfer direction pixel number $P_{TC}$ of the correction detector TD2 is examined. In this case, a condition that the transfer direction pixel numbers $P_{TI}$ and $P_{TC}$ of the inspection detector TD1 and the correction detector TD2 and the transfer cycles $\tau_{TI}$ and $\tau_{TC}$ of the inspection detector TD1 and the correction detector TD2 should satisfy in order to minimize the error in the luminance unevenness correction is examined.

In the first embodiment, part of the illumination light L11 is used for the correction detector TD2. Therefore, the correction detector TD2 is illuminated by light that is more concentrated than the light for the inspection detector TD1. Here, it is assumed that the correction detector TD2 is illuminated by light that is concentrated R times compared to the light for the inspection detector TD1. That is, it is assumed the magnification of the image data of the inspection target is R times the magnification of the image data of the luminance distribution.

In order to accurately correct luminance unevenness, both the inspection detector TD1 and the correction detector TD2 have to have the same field of view. In the case in which a TDI sensor having the same pixel size is used for each of the inspection detector TD1 and the correction detector TD2, the below-shown Expression (7) is derived from the transfer direction pixel number $P_{TI}$ of the inspection detector TD1 and the transfer direction pixel number $P_{TC}$ of the correction detector.

$$P_{TI} = P_{TC} \times R \quad (7)$$

Even when the transfer direction pixel numbers $P_{TI}$ and $P_{TC}$ of the inspection detector TD1 and the correction detector TD2 differ from each other, the inspection detector TD1 and the correction detector TD2 have to satisfy the above-described condition for the TDI detector. When the light source 11 emits light every time the correction detector TD2 performs transfers $M_C$ times and emits exactly N times within the cumulative time period $\tau_I$ of the correction detector TD2, the transfer direction pixel number $P_{TC}$ of the correction detector TD2 satisfies the following Expression (8).

$$P_{TC} = M_C \times N \quad (8)$$

The transfer cycle $\tau_{TC}$ of the correction detector TD2 satisfies the following Expression (9).

$$\tau_{TC} = \tau_S / M_C \quad (9)$$

Then, the transfer direction pixel number $P_{TI}$ of the inspection detector TDI satisfies the following Expression (10).

$$P_{TI} = R \times M_C \times N \quad (10)$$

Note that since the cumulative time periods of the inspection detector TDI and the correction detector TD2 have to be equal to each other, the transfer cycle $\tau_{TI}$ of the inspection detector TDI is one Rth (i.e., 1/R) of the transfer cycle $\tau_{TC}$ of the correction detector TD2.

$$\tau_{TI} = \tau_{TC}/R = \tau_S/(M_C \times R) \quad (11)$$

Under the above-described conditions, when the light emission cycle of pulsed light of the light source 11 is represented by $\tau_S$; the number of times the light source 11 emits light within the cumulative time period TI of the TDI detection is represented by N; and the optical magnification ratio between the inspection detector TD1 and the correction detector TD2 is represented by R, the transfer direction pixel number $P_{TC}$ and the transfer cycle $\tau_{TC}$ of the correction detector TD2 are set so that the below-shown expressions are satisfied.

$$P_{TC} = M_C \times N \quad (12)$$

$$\tau_{TC} = \tau_S / M_C \quad (13)$$

Further, the error in the luminance unevenness correction can be minimized by determining the transfer direction pixel number $P_{TI}$ and the transfer cycle $\tau_{TI}$ of the inspection detector TD1 by the following Expressions (14) and (15).

$$P_{TI} = R \times M_C \times N \quad (14)$$

$$\tau_{TI} = \tau_{TC}/R = \tau_S/(M_C \times R) \quad (15)$$

Specifically, for example, when the light emission cycle $\tau_S$ of pulsed light of the light source 11 is 200 [µs] ($\tau_S$=200 [µs]); the number N of times of light emissions of pulsed lights within the cumulative time period TI of the inspection detector TD1 and the correction detector TD2 is 42 (N=42); the optical magnification ratio R between the inspection detector TD1 and the correction detector TD2 is 4 (R=4); and the integer $M_C$ is 16 ($M_C$=16), the transfer direction pixel number $P_{TC}$ and the transfer cycle $\tau_{TC}$ of the correction detector TD2 are determined by the following Expressions (16) and (17).

$$P_{TC}=M_C \times N=16 \times 42=672 \qquad (16)$$

$$\tau_{TC}=\tau_S/M_C=200/16=12.5 \ [\mu s](80 \ [kHz]) \qquad (17)$$

The transfer direction pixel number $P_{TT}$ and the transfer cycle $\tau_{TT}$ of the inspection detector TD1 are determined by the following Expressions (18) and (19).

$$P_{TT}=R \times M_C \times N=4 \times 16 \times 42=2,688 \qquad (18)$$

$$\tau_{TT}=\tau_S/(M_C \times R)=200/16 \times 4=3.125 \ [\mu s](320 \ [kHz]) \qquad (19)$$

In this way, the transfer direction pixel number $P_{TC}$ and the transfer cycle $\tau_{TC}$ of the correction detector TD2 are determined. In the above-described example, the number of times the light source 11 emits pulsed light within the cumulative time period of the inspection detector TD1 and the correction detector TD2 is 42 for both of the detectors. Therefore, it is possible to prevent or minimize the error which would otherwise be caused by the difference between the numbers of pulses when luminance unevenness is corrected.

Figure 12:
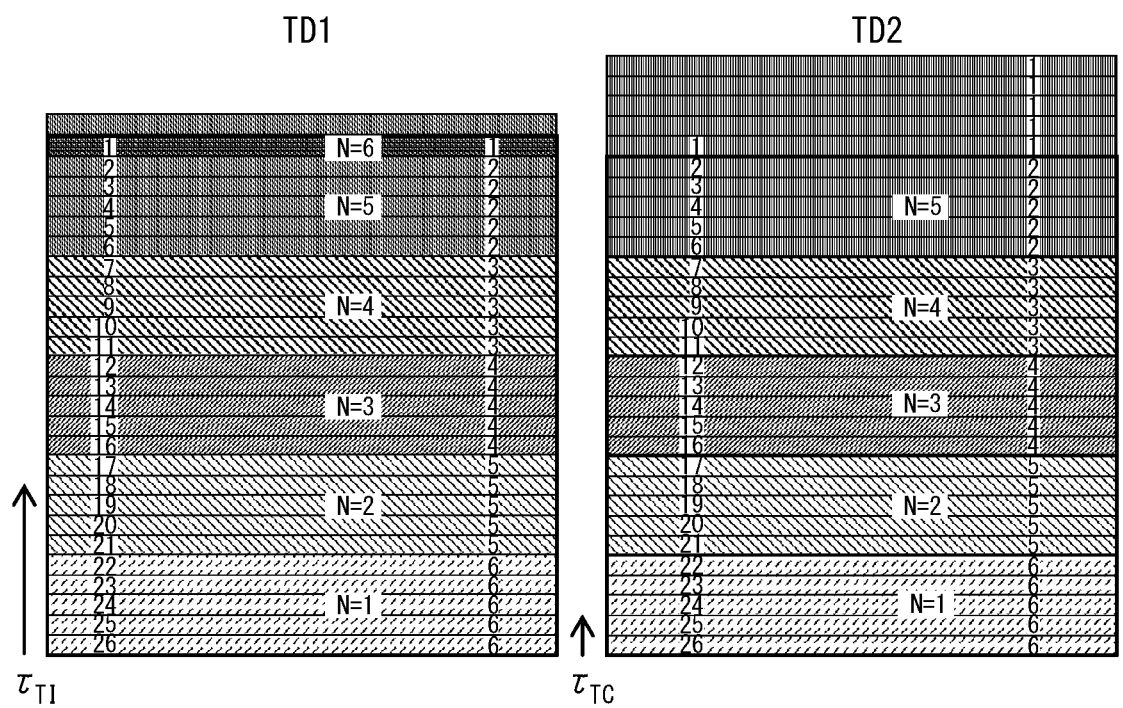
FIG. 12 shows an example of operations of an inspection detector and a correction detector according to a comparative example by using a simplified model.
Figure 13:
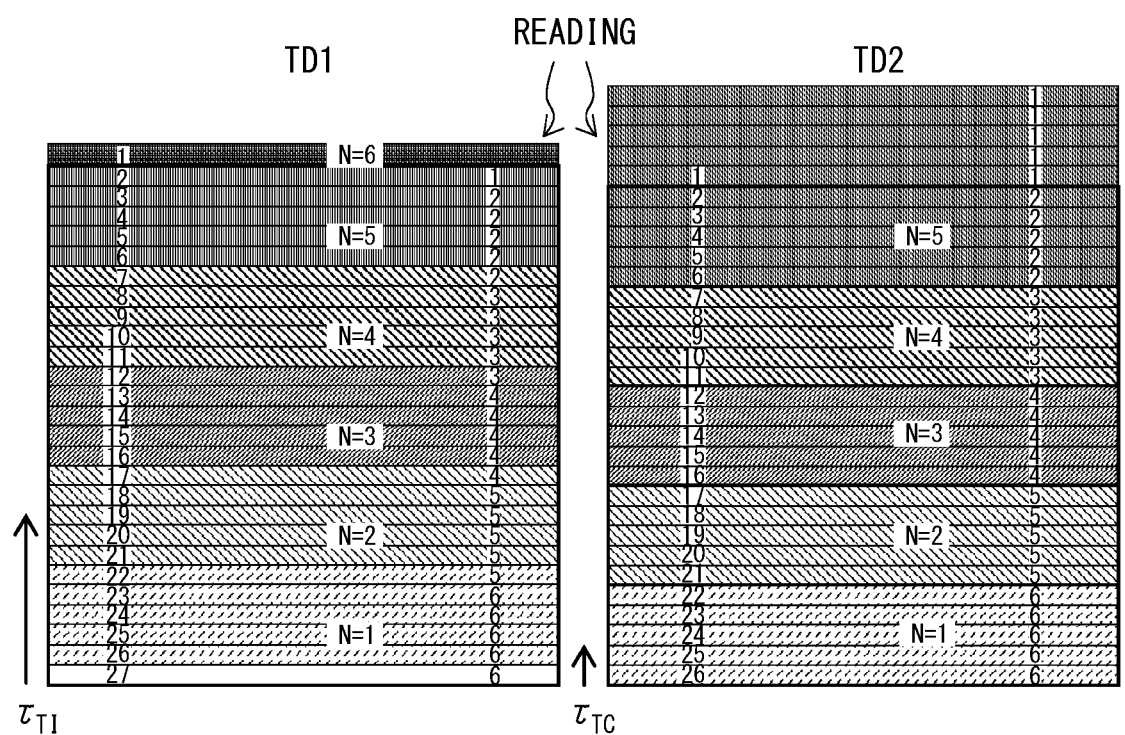
FIG. 13 shows an example of operations of an inspection detector and a correction detector according to a comparative example by using a simplified model.

Simplified models for explaining the above-described error caused by the difference between the numbers of pulses are described with reference to FIGS. 6 to 13. FIGS. 6 to 11 show examples of operations of the inspection detector and the correction detector according to the first embodiment by using simplified models. FIGS. 12 and 13 show examples of operations of an inspection detector and a correction detector according to a comparative example by using simplified models.

Firstly, a case in which each of the transfer direction pixel numbers $P_{TT}$ and $P_{TC}$ of the inspection detector TD1 and the correction detector TD2 can be divided by the number N of pulses (i.e., the remainder of the division is zero) is described.

Figure 6:
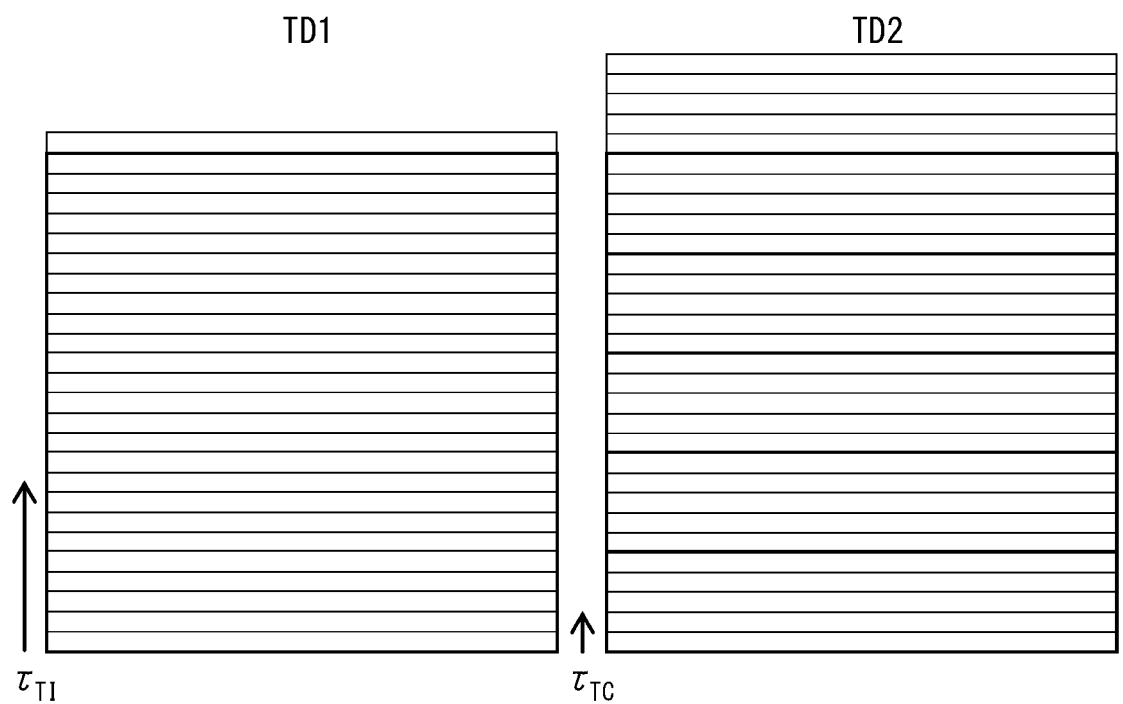
FIG. 6 shows an example of operations of an inspection detector and a correction detector according to the first embodiment by using a simplified model.

As shown in FIG. 6, it is assumed that the transfer direction pixel number $P_{TT}$ of the inspection detector TD1 is 25 ($P_{TT}=25$) and the transfer direction pixel number $P_{TC}$ of the correction detector TD2 is 5 ($P_{TC}=5$). Further, the model is simplified by defining parameters as follows: the light emission cycle $\tau_S$ of the light source 11 is 5 ($\tau_S=5$); the transfer cycle $\tau_{TT}$ of the inspection detector TD1 is 1 ($\tau_{TT}=1$); and the transfer cycle $\tau_{TC}$ of the correction detector TD2 is 5 ($\tau_{TC}=5$). The actual pixel sizes of the inspection detector TD1 and the correction detector TD2 are equal to each other. However, in the figure, the pixel size in the transfer direction of the correction detector TD2 is five times as large as the pixel size of the transfer direction.

Figure 7:
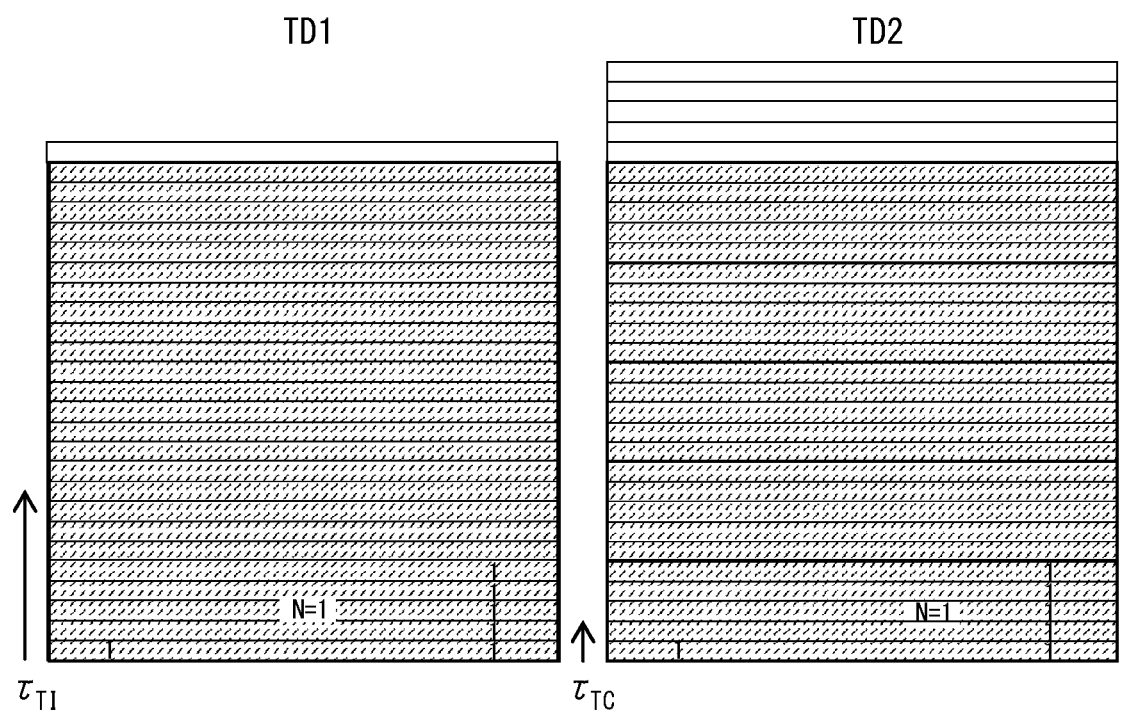
FIG. 7 shows an example of operations of an inspection detector and a correction detector according to the first embodiment by using a simplified model.
Figure 8:
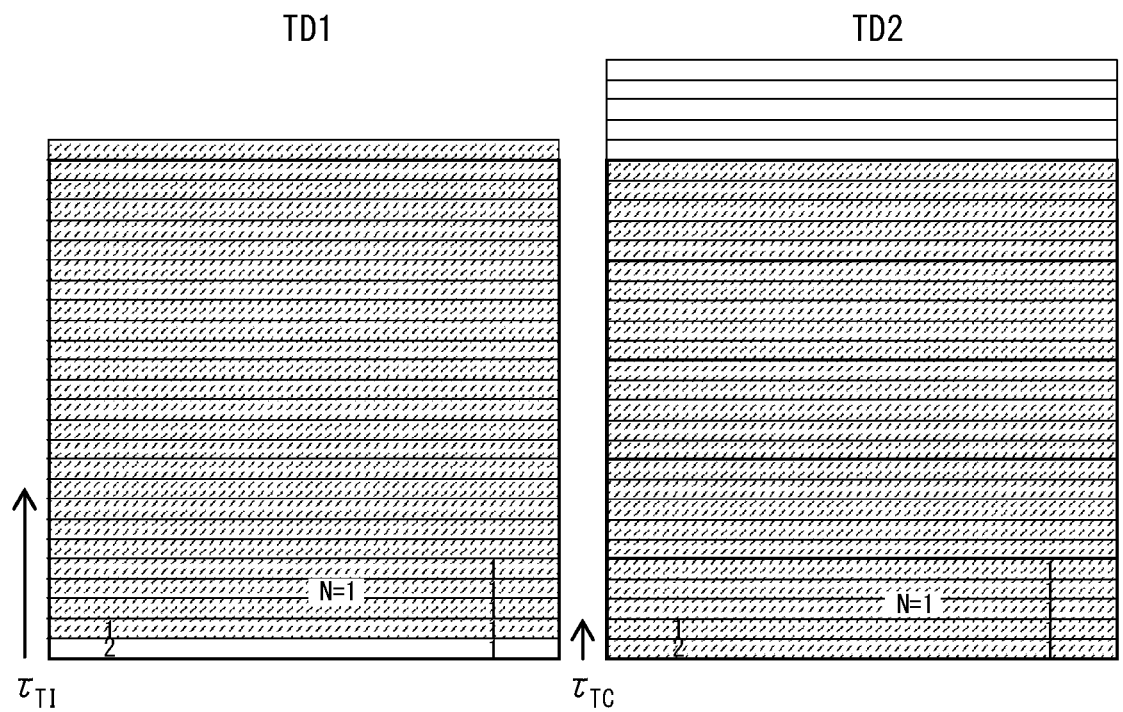
FIG. 8 shows an example of operations of an inspection detector and a correction detector according to the first embodiment by using a simplified model.
Figure 9:
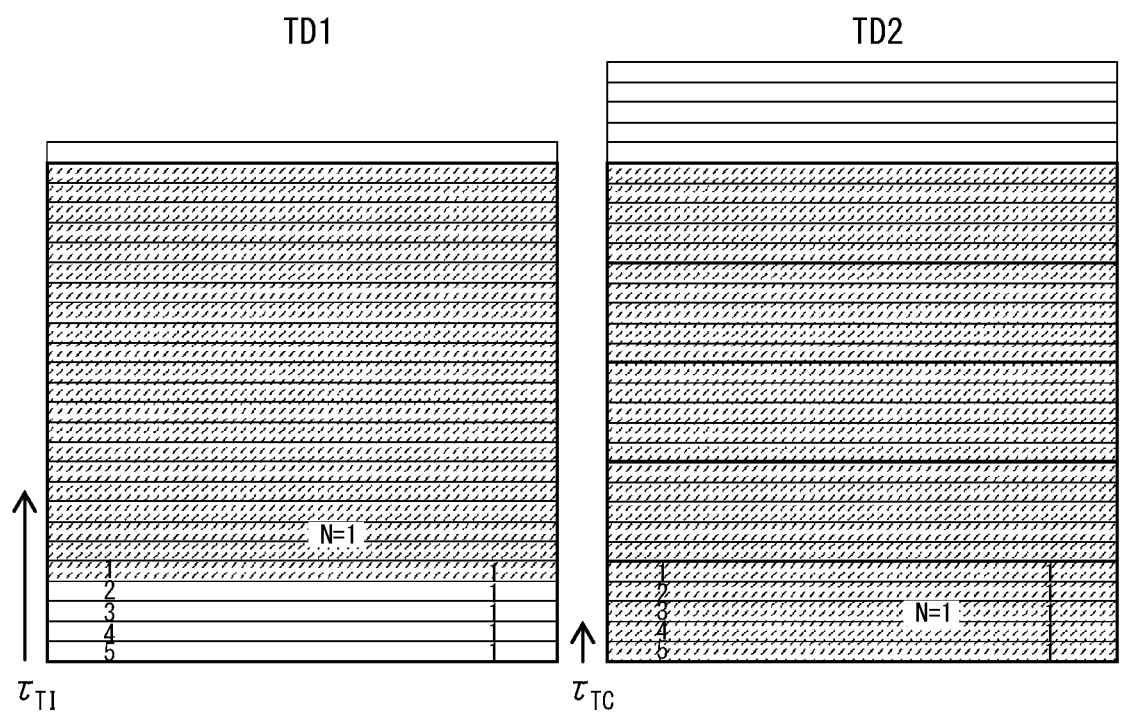
FIG. 9 shows an example of operations of an inspection detector and a correction detector according to the first embodiment by using a simplified model.

As shown in FIG. 7, at a time t=1, by a light emission of the first pulsed light by the light source 11, each pixel of the inspection detector TD1 and the correction detector TD2 receives one pulsed light (i.e., N=1). Next, as shown in FIG. 8, at a time t=2, the inspection detector TD1 transfers electrical charges accumulated in the pixels in the transfer direction by one row. For example, the inspection detector TD1 transfers electrical charged in the first row of the pixels to the second row. A part that has received no pulse (i.e., N=0) is formed in the first row of the pixels. Then, as shown in FIG. 9, at a time t=5, part that has received no pulse (i.e., N=0) is formed in the first to fourth rows of the inspection detector TD1.

Figure 10:
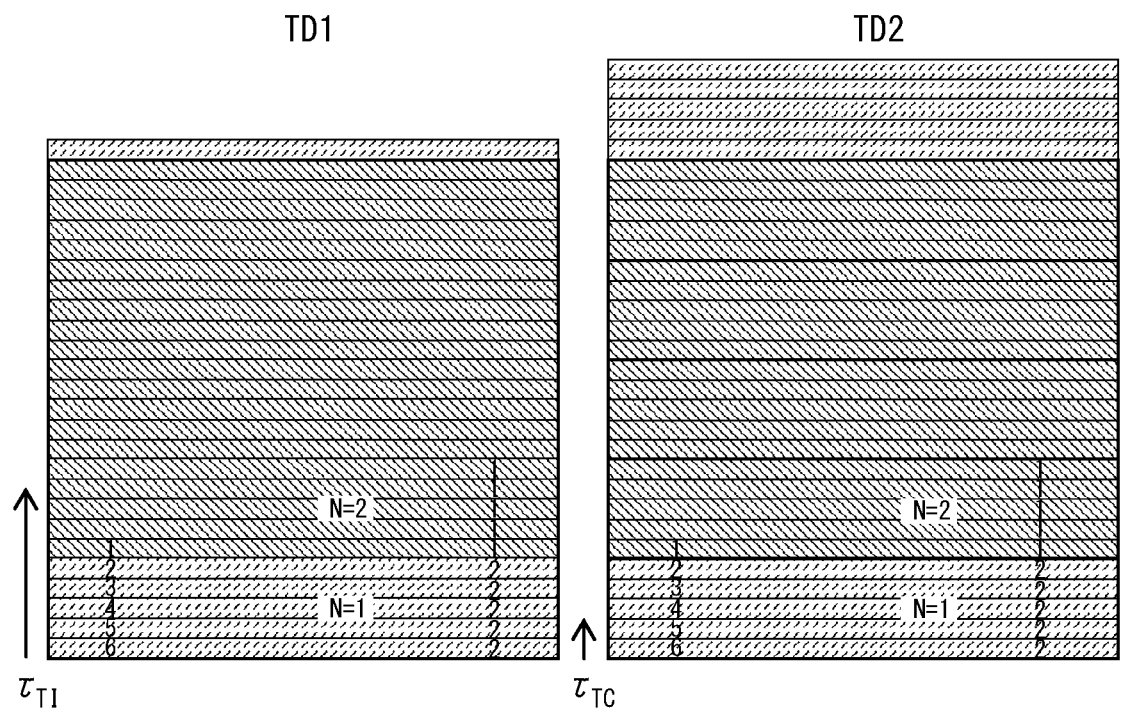
FIG. 10 shows an example of operations of an inspection detector and a correction detector according to the first embodiment by using a simplified model.

As shown in FIG. 10, after a time t=1 has further relapsed, i.e., at a time t=6, the inspection detector TD1 transfers electrical charges accumulated in the pixels in the transfer direction by one row. The correction detector TD2 also transfers electrical charges accumulated in the pixels in the transfer direction by one row. At this point, the second pulsed light is emitted in synchronization with the inspection detector TD1 and the correction detector TD2. As a result, pixels in the lowest five rows of the inspection detector TD1 receive the first pulsed light (i.e., receive pulsed light for the first time). The pixels in the rows other than the lowest five rows of the inspection detector TD1 receive pulsed light corresponding to two times of light emissions. Meanwhile, the pixels in the lowest row of the correction detector TD2 receive the first pulsed light (i.e., receive pulsed light for the first time). The pixels in the rows other than the lowest row of the correction detector TD2 receive pulsed light corresponding to two times of light emissions. In this manner, pulsed light is emitted every time the inspection detector TD1 transfers electrical charges by five rows and every time the correction detector TD2 transfers electrical charges by one row.

Figure 11:
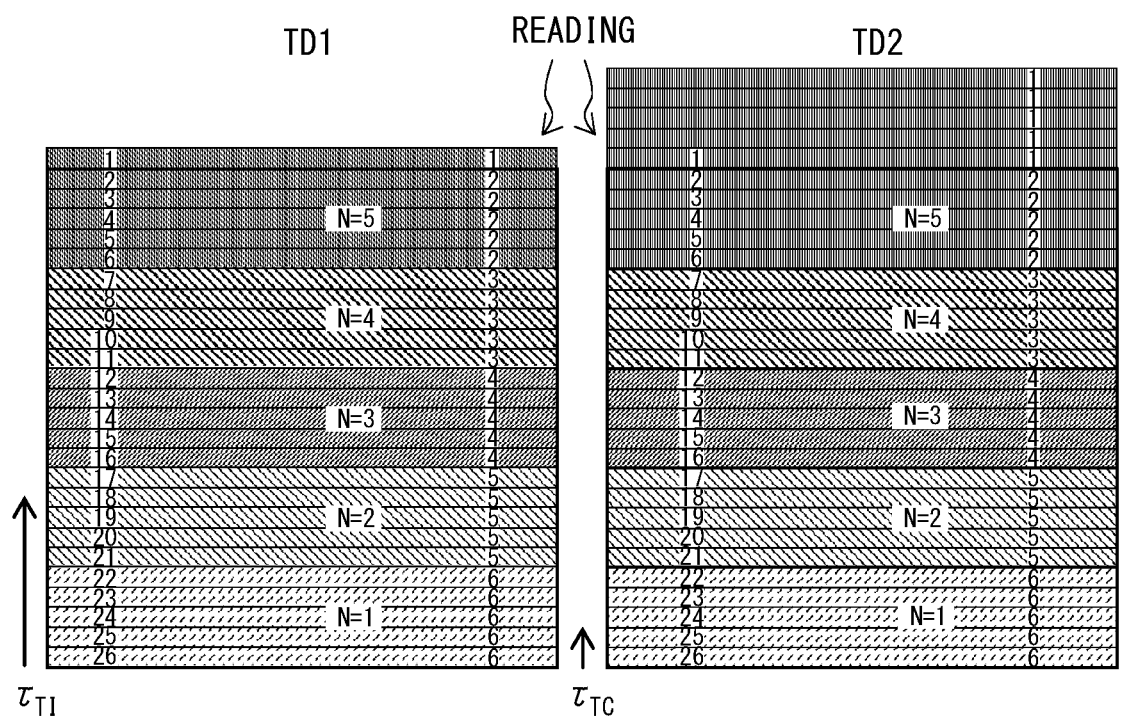
FIG. 11 shows an example of operations of an inspection detector and a correction detector according to the first embodiment by using a simplified model.

As shown in FIG. 11, at a time t=26, image data is read from the inspection detector TD1 and the correction detector TD2. Image data that have been obtained by receiving the same number of pulsed lights are read from the inspection detector TD1 and the correction detector TD2. Therefore, it is possible to prevent or minimize an error which would otherwise be caused by the difference between the numbers of pulses.

Next, as a comparative example, a case in which the transfer direction pixel number $P_{TT}$ of the inspection detector TD1 cannot be divided by the number N of pulses (i.e., the remainder of the division is not zero) is described. As shown in FIG. 12, in a case in which the transfer direction pixel number $P_{TT}$ of the inspection detector TD1 is set to 26 ($P_{TT}=26$), the transfer direction pixel number $P_{TC}$ of the correction detector TD2 is set to 5 ($P_{TC}=5$) and the light emission cycle $\tau_S$ of the light source 11 is set to 5 ($\tau_S=5$). Further, the transfer cycle $\tau_{TT}$ of the inspection detector TD1 is set to 1 ($\tau_{TT}=1$) and the transfer cycle $\tau_{TC}$ of the correction detector TD2 is set to 5 ($\tau_{TC}=5$). In this case, the relations $P_{TT}=R \times M_C \times N$ and $\tau_{TT}=\tau_S/(M_C \times R)$ cannot be satisfied.

As shown in FIG. 12, at a time t=26, the sixth pulsed light is emitted. In this case, the pixels in the 26th row of the inspection detector TD1 receive the sixth pulsed light. Meanwhile, the correction detector TD2 outputs image data and there is no pixel that receives the sixth pulsed light. Further, as shown in FIG. 13, at a time t=27, the inspection detector TD1 outputs image data that has been obtained by receiving pulsed lights six times. Meanwhile, the correction detector TD2 outputs image data that has been obtained by receiving pulsed lights five times.

As described above, when the transfer direction pixel number $P_{TT}$ of the inspection detector TD1 is cannot be divided by the number N of pulses, image data that is obtained by accumulating signals of the number of pulsed lights equal to the quotient of the division of the cumulative time period $\tau_I$ by the emission cycle $\tau_S$ (i.e., N=5) and image data that is obtained by accumulating signals of the number of pulsed lights greater than the quotient by one (i.e., N=6) are periodically (i.e., alternately) output. Therefore, when the transfer direction pixel number and the transfer cycle do not satisfy the predetermined relation as in the case of the comparative example, the error caused by the difference between the numbers of pulses cannot be prevented.

In this embodiment, the transfer direction pixel number and the transfer cycle are adjusted so that they satisfy the predetermined relation. Further, inspection image data is detected by correcting image data of the inspection target based on image data of the luminance distribution that is acquired under the aforementioned condition.

Next, as shown in a step S14 in FIG. 3, the inspection target is inspected by using the inspection image data. Specifically, the processing unit 40 inspects the inspection target by using the inspection image data detected by correcting the above-described image data of the inspection target. After that, the process is finished. In this manner, the inspection apparatus 1 can inspect the inspection target.

Next, advantageous effects of this embodiment are described. In this embodiment, image data of the luminance distribution of the illumination light L11 is acquired by the correction detector TD2 and image data of the inspection target is corrected by using the acquired image data of the luminance distribution. Therefore, it is possible to accurately detect the image data of the inspection target.

Further, the magnification of the image data of the luminance distribution is made lower than the magnification of the image data of the inspection target. In this way, it is possible to increase an amount of light for detecting the luminance distribution and thereby to accurately correct the luminance distribution of the illumination light L11.

The light emission timing of the pulsed light source is controlled so that it does not coincide with the transfer timing of the inspection detector and the correction detector. That is, synchronization control is performed so that the transfer timing of the inspection detector and the correction detector and the light emission timing of the light source have a certain phase difference therebetween. In this way, it is possible to prevent an error that would otherwise occur due to the difference between the numbers of pulses of light emitted within the cumulative time period of the detector.

Further, the transfer direction pixel numbers $P_{TI}$ and $P_{TC}$ and the transfer cycles $\tau_{TI}$ and $\tau_{TC}$ of the inspection detector TD1 and the correction detector TD2 are determined so that they satisfy the predetermined relation. In this way, it is possible to prevent or minimize an error that would otherwise occur due to the difference between the numbers of pulses of light emitted within the cumulative time period in the luminance unevenness correction.

Part of the illumination light L11 is taken out by the cut mirror and detected by the correction detector TD2. In this way, it is possible to prevent or minimize the influence on the illumination light L11 used for the inspection and thereby to accurately inspect the object.

Further, in a cross-sectional area in a cross section of the illumination light L11 perpendicular to its optical axis 15, a cross-sectional area of part of the illumination light L11 is made smaller than a cross-sectional area of the other part of the illumination light L11. In this way, it is possible to prevent or minimize the influence on the illumination light L11 used for the inspection and thereby to accurately inspect the object.

Second Embodiment

Figure 14:
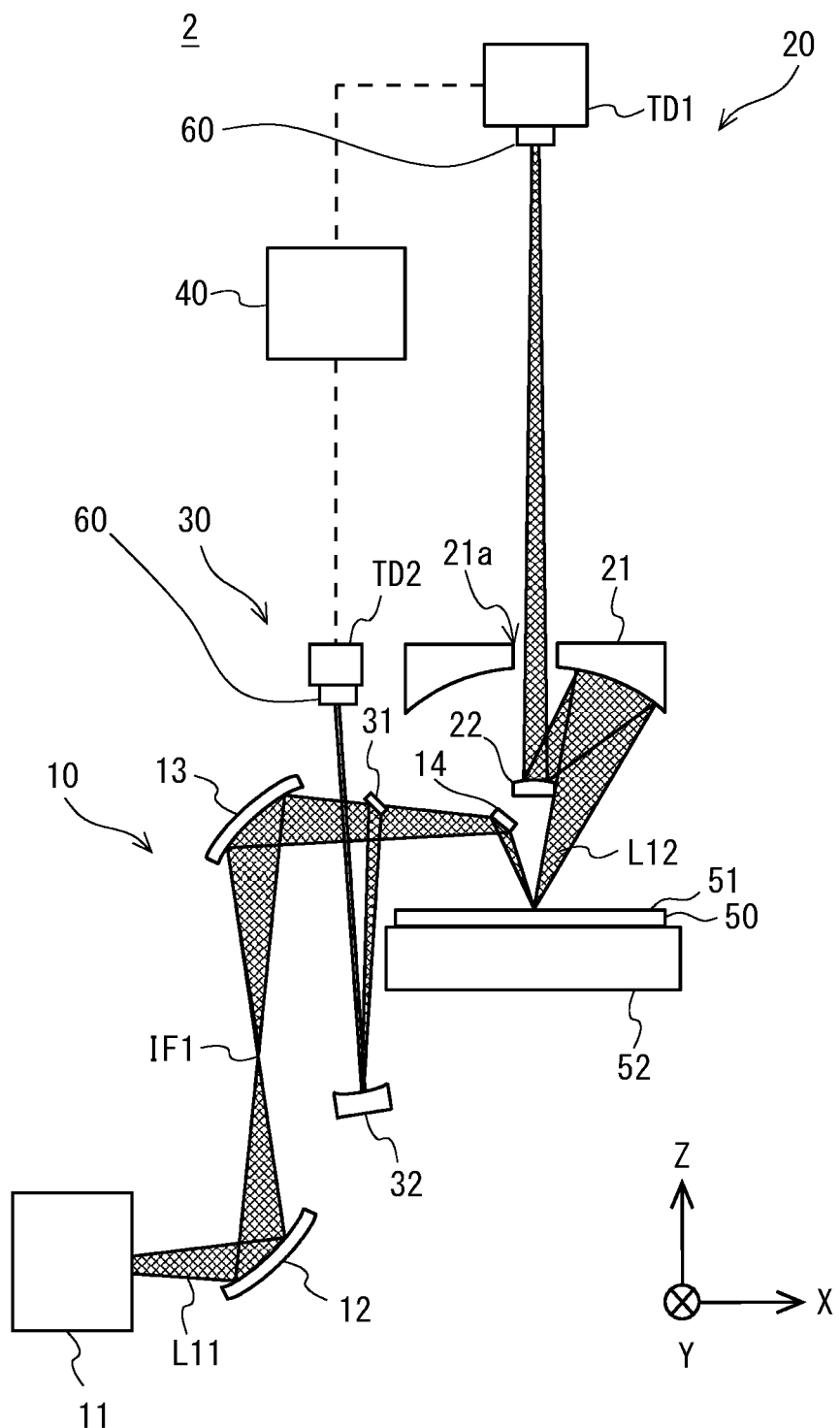
FIG. 14 shows an example of a configuration of an inspection apparatus according to a second embodiment.

Next, an inspection apparatus 2 according to a second embodiment is described. The inspection apparatus 2 according to this embodiment includes a light-shielding unit. FIG. 14 shows an example of a configuration of the inspection apparatus according to the second embodiment. As shown in FIG. 14, in the inspection apparatus 2, a light-shielding unit 60 is disposed on a surface of the inspection detector TD1 on which reflected light L12 is incident, and another light-shielding unit 60 is disposed on a surface of the correction detector TD2 on which illumination light L11 is incident. The rest of the configuration is the same as that of the inspection apparatus 1 according to the first embodiment.

In general, the transfer direction pixel number of a TDI detector is determined by a fixed light-shielding plate. Therefore, it is difficult to set the transfer direction pixel number to an arbitrary number. Further, in the operation of an ordinary TDI detector, even if there is an error in the order of several pixels to several tens of pixels in the set transfer direction pixel number, the ratio of the error to the total number of pixels is small. Therefore, its influence on the accumulated electrical charges is small.

However, when luminance unevenness is corrected by using the inspection detector TDI and the correction detector TD2 as in the case of the first embodiment, it is desirable to prevent or minimize the error even when the error is in the order of several pixels to several tens of pixels to the set transfer direction pixel number. Therefore, in this embodiment, light-shielding units 60 that set the transfer direction pixel numbers of the inspection detector TD1 and the correction detector TD2 with an accuracy of 0.1 pixels or less are introduced.

Figure 15:
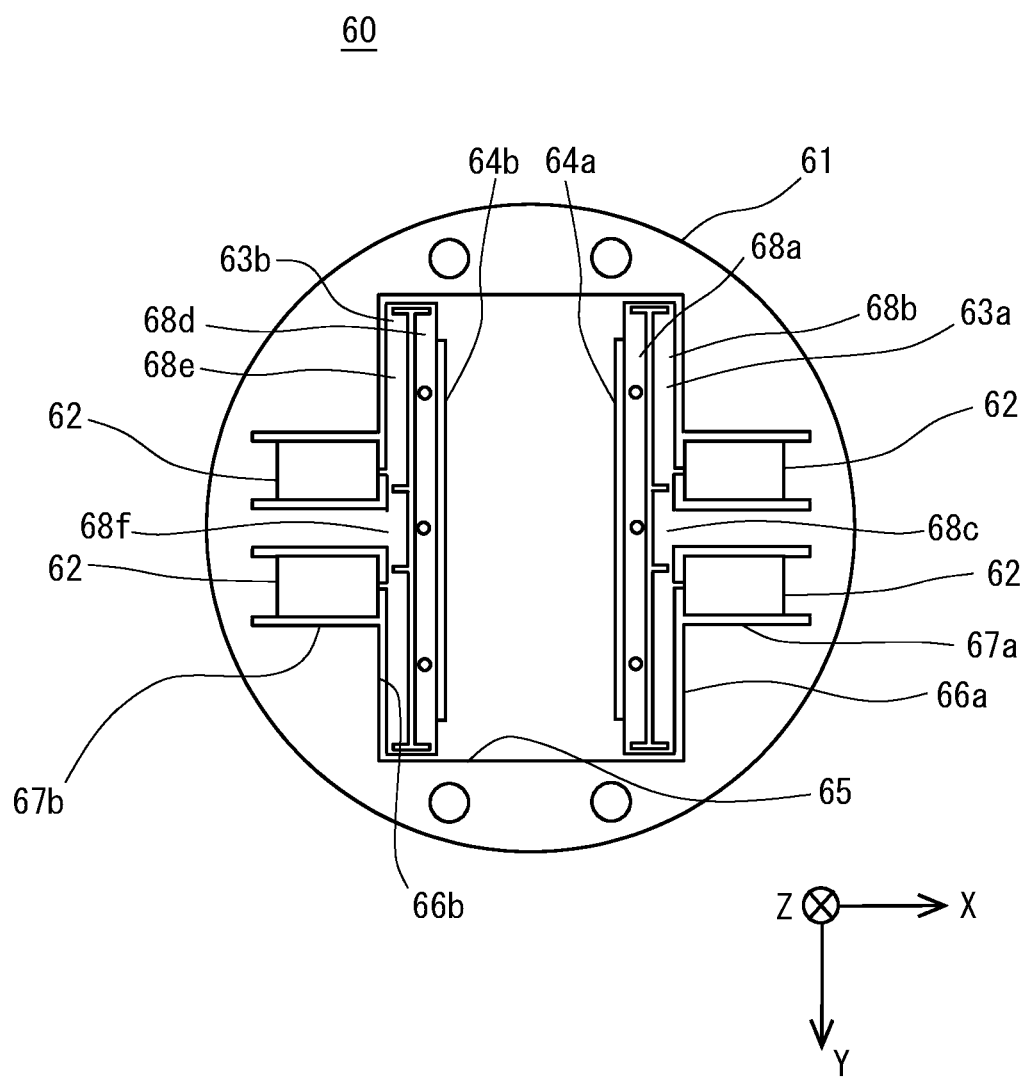
FIG. 15 is a plan view showing an example of a light-shielding unit of the inspection apparatus according to the second embodiment.
Figure 16:
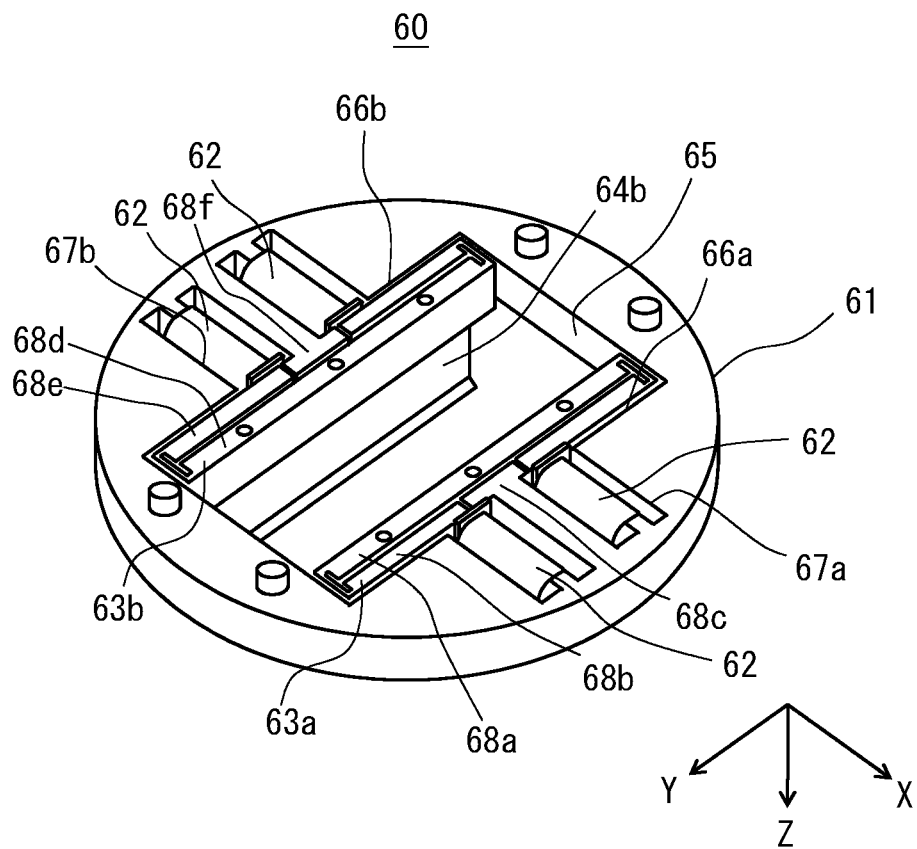
FIG. 16 is a perspective view showing an example of a light-shielding unit of the inspection apparatus according to the second embodiment.

FIG. 15 is a plan view showing an example of the light-shielding unit 60 of the inspection apparatus 2 according to the second embodiment. FIG. 16 is a perspective view showing an example of the light-shielding unit 60 of the inspection apparatus 2 according to the second embodiment. As shown in FIGS. 15 and 16, the light-shielding unit 60 includes a main body part 61, piezo elements 62, fine positioners 63a and 63b, and light-shielding plates 64a and 64b.

The main body part 61 is a disk-shaped member and a substantially rectangular opening 65 is formed in its center. The short-side direction of the opening 65 is defined as an X-axis direction and the long-side direction thereof is defined as a Y-axis direction. Recesses 67a and 67b are formed in central parts of two sides 66a and 66b of the opening 65, which are opposed to each other in the X-axis direction. A plurality of piezo elements 62 are disposed in the recesses 67a and 67b.

Fine positioners 63a and 63b are disposed along the sides 66a and 66b, respectively. The fine positioner 63a has a flexure structure in which beams 68a and 68b extending in the Y-axis direction are combined with a fixed part 68c extending in the X-axis direction. Ends of the beams 68a and 68b of the fine positioner 63a on the Y-axis positive direction side are connected to each other and the ends on the Y-axis negative direction side are connected to each other. Further, an end of the fixed part 68c on the X-axis negative direction side is connected to a central part of the beam 68b and an end of the fixed part 68c on the X-axis positive direction side is connected to a central part of the recess 67a.

The fine positioner 63b has a flexure structure in which beams 68d and 68e extending in the Y-axis direction are combined with a fixed part 68f extending in the X-axis direction. Ends of the beams 68d and 68e of the fine positioner 63b on the Y-axis positive direction side are connected to each other and the ends on the Y-axis negative direction side are connected to each other. Further, an end of the fixed part 68f on the X-axis positive direction side is connected to a central part of the beam 68e and an end of the fixed part 68f on the X-axis negative direction side is connected to a central part of the recess 67b.

Figure 17:
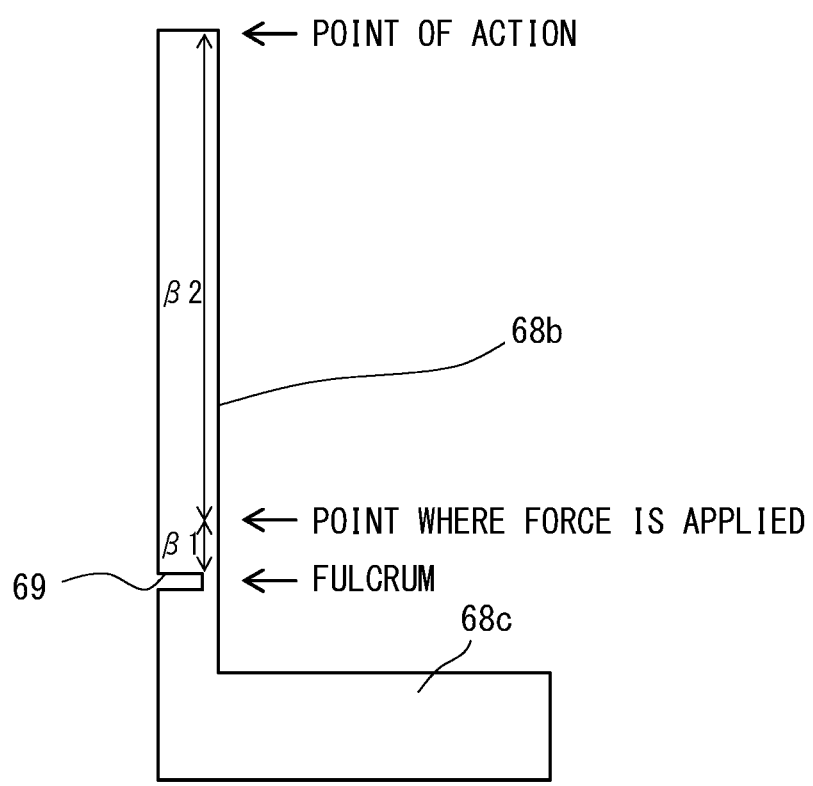
FIG. 17 is an enlarged view showing an example of a part of a light-shielding unit of the inspection apparatus according to the second embodiment.

FIG. 17 is an enlarged view showing an example of a part of the light-shielding unit 60 of the inspection apparatus 2 according to the second embodiment. As shown in FIG. 17, a notch 69 is formed on the beam 68b of the fine positioner 63a on the Y-axis positive direction side on the side 66a of the opening 65. Therefore, the beam is moved by the operation of the piezo element 62 while using a part between the notch 69 and the end of the beam 68b as a point where a force is applied. In this way, the beam is moved in the X-axis direction by the principle of leverage in which the notch 69 acts as a fulcrum and the end of the beam 68b acts as a point of action. A leverage ratio $\alpha=(\beta1+\beta2)/\beta1$ can be increased by bringing the notch 69 closer to the point where the force is applied. It is possible to maintain the direction of the displacement unchanged even when the leverage ratio is changed. A similar structure is also formed in each of the Y-axis negative side on the side 66a of the opening 65, and the Y-axis positive side and the Y-axis negative side on the side 66b of the opening 65.

The light-shielding plate 64a is attached to the beam 68a of the fine positioner 63a disposed along the side 66a. The light-shielding plate 64b is attached to the beam 68d of the fine positioner 63b arranged along the side 66b. The beams 68b and 68e are moved by operating the piezo element 62. In this way, the light-shielding plates 64a and 64b define the width of the opening 65 in the X-axis direction.

The light-shielding unit 60 according to this embodiment includes fine positioners 63a and 63b. The fine positioners 63a and 63b can control the positions of the beams 68a and 68d to which the light-shielding plates 64a and 64b are attached by using the two piezo elements 62. Further, the fine positioners 63a and 63b can adjust the angle of the light-shielding plates 64a and 64b with respect to the X-axis direction, in addition moving the light-shielding plates 64a and 64b in the X-axis direction. Further, the fine positioners 63a and 63b can define the positions of the pixels on both ends in the transfer direction. The width of the light-shielding plates 64a and 64b can be adjusted while monitoring image data of the inspection detector TD1 and the correction detector TD2.

The operating range of the fine positioners 63a and 63b in the X-axis direction is about 100 [μm] and its positioning accuracy is 1 [μm] or less. Therefore, it is possible to accurately control the number of pixels in the transfer direction in which pixels having a size of about 10 [μm] are arranged in the transfer direction.

As describe above, the inspection apparatus 2 according to this embodiment further includes the light-shielding unit 60 that adjusts the transfer direction pixel numbers of the inspection detector TD1 and the correction detector TD2 by using the light-shielding plates 64a and 64b attached to the fine positioners 63a and 63b. Therefore, it is possible to set the transfer direction pixel numbers $P_{TT}$ and $P_{TC}$ of the inspection detector TD1 and the correction detector TD2 to predetermined numbers and thereby to prevent or minimize the error in the luminance unevenness correction. Other advantageous effects are already described in the first embodiment.

Although the first and second embodiments according to the present disclosure have been explained above, the present disclosure also includes various modifications that do not substantially impair the purposes and the advantages of the present disclosure. Further, the above-described embodiments should not be used to limit the scope of the present disclosure.

The first and second embodiments can be combined as desirable by one of ordinary skill in the art.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

The invention claimed is:

1. A detection method comprising:
    illuminating an object to be inspected by using illumination light including pulsed light;
    acquiring image data of the object to be inspected by concentrating light from the object to be inspected illuminated by the illumination light and detecting the concentrated light by an inspection detector;
    acquiring image data of a luminance distribution of the illumination light, the luminance distribution being detected by illuminating a correction detector by using part of the illumination light; and
    detecting inspection image data by correcting the image data of the object to be inspected based on the image data of the luminance distribution.

2. The detection method according to claim 1, wherein a magnification of the image data of the luminance distribution is made lower than a magnification of the image data of the object to be inspected.

3. The detection method according to claim 1, wherein a light emission timing of a light source that emits illumination light including pulsed light is synchronously controlled so that it does not coincide with a transfer timing of the inspection detector and the correction detector.

4. The detection method according to claim 1, wherein a transfer direction pixel number $P_{TC}$ and a transfer cycle $\tau_{TC}$ of the correction detector are determined so that relations $P_{TC}=M_C \times N$ and $\tau_{TC}=\tau_S/M_C$ are satisfied,
    wherein $\tau_S$ is a light emission cycle of the pulsed light; N is the number of times the pulsed light is emitted within a cumulative time period of image data of the inspection detector, and $M_C$ is an integer.

5. The detection method according to claim 4, wherein a transfer direction pixel number $P_{TT}$ and a transfer cycle $\tau_{TT}$ of the inspection detector are determined so that relations $P_{TT}=R \times M_C \times N$ and $T_{TT}=\tau_S/(M_C \times R)$ are satisfied,
    wherein R is a magnification of the image data of the object to be inspected relative to a magnification of the image data of the luminance distribution.

6. The detection method according to claim 4, wherein the transfer direction pixel numbers of the inspection detector and the correction detector are adjusted by using a light-shielding plate attached to a fine positioner.

7. The detection method according to claim 1, wherein in the acquiring of the image data of the luminance distribution of the illumination light, part of the illumination light is taken out between a dropping mirror and a reflecting mirror by using a cut mirror, the dropping mirror being configured to make the illumination light incident on the object to be inspected, the reflecting mirror being configured to convert the illumination light into converged light and make the converged light incident on the dropping mirror.

8. The detection method according to claim 7, wherein in a cross-sectional area in a cross section of the illumination light perpendicular to its optical axis in a place where the cut mirror is disposed, a cross-sectional area of the part of the illumination light is made smaller than a cross-sectional area of the other part of the illumination light.

9. An inspection method comprising:
    illuminating an object to be inspected by using illumination light including pulsed light;
    acquiring image data of the object to be inspected by concentrating light from the object to be inspected illuminated by the illumination light and detecting the concentrated light by an inspection detector;

acquiring image data of a luminance distribution of the illumination light, the luminance distribution being detected by illuminating a correction detector by using part of the illumination light;

detecting inspection image data by correcting the image data of the object to be inspected based on the image data of the luminance distribution; and inspecting the object to be inspected by using the inspection image data.

10. A detection apparatus comprising:

an illumination optical system configured to illuminate an object to be inspected by using illumination light including pulsed light;

a detection optical system configured to acquire image data of the object to be inspected by concentrating light from the object to be inspected illuminated by the illumination light and detecting the concentrated light by an inspection detector;

a monitor unit configured to acquire image data of a luminance distribution of the illumination light, the luminance distribution being detected by illuminating a correction detector by using part of the illumination light; and a processing unit configured to detect inspection image data by correcting the image data of the object to be inspected based on the image data of the luminance distribution.

11. The detection apparatus according to claim 10, wherein a magnification of the image data of the luminance distribution acquired by the monitor unit is made lower than a magnification of the image data of the object to be inspected acquired by the detection optical system.

12. The detection apparatus according to claim 10, wherein a light emission timing of a light source that emits illumination light including pulsed light is synchronously controlled so that it does not coincide with a transfer timing of the inspection detector and the correction detector.

13. The detection apparatus according to claim 10, wherein a transfer direction pixel number $P_{TC}$ and a transfer cycle $\tau_{TC}$ of the correction detector satisfy relations $P_{TC}=M_C \times N$ and $\tau_{TC}=\tau_S/M_C$, wherein $\tau_S$ is a light emission cycle of the pulsed light, N is the number of times the pulsed light is emitted within a cumulative time period of image data of the inspection detector, and $M_C$ is an integer.

14. The detection apparatus according to claim 13, wherein a transfer direction pixel number $P_{TI}$ and a transfer cycle $\tau_{TI}$ of the inspection detector satisfy relations $P_{TI}=R \times M_C \times N$ and $T_{TI}=\tau_S/(M_C \times R)$, wherein R is the magnification of the image data of the object to be inspected relative to the magnification of the image data of the luminance distribution.

15. The detection apparatus according to claim 13, further comprising a light-shielding unit configured to adjust the transfer direction pixel numbers of the inspection detector and the correction detector by using a light-shielding plate attached to a fine positioner.

16. The detection apparatus according to claim 10, wherein the illumination optical system comprises a dropping mirror configured to make the illumination light incident on the object to be inspected, and a reflecting mirror configured to convert the illumination light into converged light and make the converged light incident on the dropping mirror, and the monitor unit comprises a cut mirror configured to take out part of the illumination light between the reflecting mirror and the dropping mirror.

17. The detection apparatus according to claim 16, wherein in a cross-sectional area in a cross section of the illumination light perpendicular to its optical axis in a place where the cut mirror is disposed, a cross-sectional area of the part of the illumination light is smaller than a cross-sectional area of the other part of the illumination light.

18. An inspection apparatus comprising:

an illumination optical system configured to illuminate an object to be inspected by using illumination light including pulsed light;

a detection optical system configured to acquire image data of the object to be inspected by concentrating light from the object to be inspected illuminated by the illumination light and detecting the concentrated light by an inspection detector;

a monitor unit configured to acquire image data of a luminance distribution of the illumination light, the luminance distribution being detected by illuminating a correction detector by using part of the illumination light; and a processing unit configured to detect inspection image data by correcting the image data of the object to be inspected based on the image data of the luminance distribution, wherein the processing unit inspects the object to be inspected by using the detected inspection image data.

\* \* \* \* \*